(12) United States Patent
Lifshitz et al.

(10) Patent No.: US 10,314,671 B2
(45) Date of Patent: Jun. 11, 2019

(54) APPARATUS AND METHOD FOR ENDODONTIC TREATMENT

(71) Applicant: Fluidfile Ltd., Petach-Tikva (IL)

(72) Inventors: Amnon Lifshitz, Petach-Tikva (IL); Yehuda Darshan, Petach-Tikva (IL)

(73) Assignee: Fluidfile Ltd., Petach-Tikva (IL)

( * ) Notice: Subject to any disclaimer, the term of this patent is extended or adjusted under 35 U.S.C. 154(b) by 122 days.

(21) Appl. No.: 14/394,292

(22) PCT Filed: Apr. 15, 2013

(86) PCT No.: PCT/IL2013/050330
§ 371 (c)(1),
(2) Date: Oct. 14, 2014

(87) PCT Pub. No.: WO2013/157000
PCT Pub. Date: Oct. 24, 2013

(65) Prior Publication Data
US 2015/0125811 A1 May 7, 2015

(30) Foreign Application Priority Data
Apr. 15, 2012 (IL) .......................................... 219169

(51) Int. Cl.
*A61C 3/00* (2006.01)
*A61C 5/40* (2017.01)
(Continued)

(52) U.S. Cl.
CPC .............. *A61C 5/40* (2017.02); *A61C 1/0092* (2013.01); *A61C 3/025* (2013.01); *A61C 17/02* (2013.01);
(Continued)

(58) Field of Classification Search
CPC ........... A61C 17/02; A61C 5/40; A61C 3/025; A61C 1/0092; A61C 17/022;
(Continued)

(56) References Cited

U.S. PATENT DOCUMENTS

| 3,739,983 A | 6/1973 | Jousson |
| 4,021,921 A | 5/1977 | Detaille |

(Continued)

FOREIGN PATENT DOCUMENTS

| DE | 19645644 | 5/1998 |
| DE | 102010051227 | 5/2012 |

(Continued)

OTHER PUBLICATIONS

Office Action dated Nov. 19, 2015 From the Israel Patent Office Re. Application No. 219169 and Its Translation Into English.
(Continued)

*Primary Examiner* — Nicholas Lucchesi

(57) ABSTRACT

An apparatus for endodontic treatment, used for cleaning and/or abrading a root canal using at least one angled fluid jet. In some embodiments, the apparatus comprises a nozzle that is shaped to create one or more angled fluid jets, for example including an internal cone and an external cone. In some embodiments, the flow of fluid advances along a root canal wall for removal of soft tissue such as nerve tissue, pulp tissue, and/or debris.

24 Claims, 28 Drawing Sheets

(51) Int. Cl.
    *A61C 17/02* (2006.01)
    *A61C 3/025* (2006.01)
    *A61C 17/022* (2006.01)
    *A61C 17/06* (2006.01)
    *A61C 1/00* (2006.01)
    *A61C 1/12* (2006.01)
    *A61C 1/08* (2006.01)

(52) U.S. Cl.
    CPC ........ *A61C 17/022* (2013.01); *A61C 17/0202* (2013.01); *A61C 17/043* (2013.01); *A61C 1/0061* (2013.01); *A61C 1/087* (2013.01); *A61C 1/12* (2013.01); *A61C 17/0208* (2013.01)

(58) Field of Classification Search
    CPC ....... A61C 17/043; A61C 1/0061; A61C 1/12; A61C 1/087; A61C 17/0208
    USPC .................................................. 433/81, 224
    See application file for complete search history.

(56) References Cited

U.S. PATENT DOCUMENTS

| | | | |
|---|---|---|---|
| 4,676,749 | A | 6/1987 | Mabille |
| 5,295,828 | A * | 3/1994 | Grosrey ................ A61C 5/04 433/224 |
| 5,484,283 | A | 4/1996 | Franetzki |
| 6,224,378 | B1 | 5/2001 | Valdes et al. |
| 6,497,572 | B2 | 12/2002 | Hood et al. |
| 7,891,977 | B2 | 2/2011 | Riva |
| 8,235,719 | B2 | 8/2012 | Ruddle et al. |
| 8,297,540 | B1 | 10/2012 | Vijay |
| 8,328,552 | B2 | 12/2012 | Ruddle et al. |
| 8,388,345 | B2 | 3/2013 | Ruddle |
| 9,084,651 | B2 * | 7/2015 | Laufer ................ A61C 3/025 |
| 2001/0055742 | A1 | 12/2001 | Hood et al. |
| 2003/0129560 | A1 | 7/2003 | Atkin et al. |
| 2007/0042316 | A1 | 2/2007 | Pichat et al. |
| 2007/0248932 | A1 | 10/2007 | Gharib et al. |
| 2008/0319453 | A1 | 12/2008 | Tavger |
| 2009/0004621 | A1 | 1/2009 | Quan et al. |
| 2009/0130622 | A1 | 5/2009 | Bollinger et al. |
| 2010/0092922 | A1 | 4/2010 | Ruddle |
| 2010/0143861 | A1 | 6/2010 | Gharib et al. |
| 2010/0152634 | A1 | 6/2010 | Dove |
| 2010/0233649 | A1 | 9/2010 | McPeek et al. |
| 2010/0272764 | A1 | 10/2010 | Latta et al. |
| 2011/0111365 | A1 | 5/2011 | Gharib et al. |
| 2011/0117517 | A1 | 5/2011 | Bergheim et al. |
| 2011/0183284 | A1 | 7/2011 | Yamanaka et al. |
| 2011/0189630 | A1 * | 8/2011 | Koubi ..................... A61C 5/04 433/81 |
| 2012/0141953 | A1 | 6/2012 | Mueller |
| 2012/0237893 | A1 | 9/2012 | Bergheim et al. |
| 2012/0276497 | A1 | 11/2012 | Gharib et al. |
| 2013/0040267 | A1 | 2/2013 | Bergheim et al. |
| 2014/0080090 | A1 | 3/2014 | Laufer |
| 2015/0044631 | A1 | 2/2015 | Lifshitz et al. |
| 2016/0095679 | A1 | 4/2016 | Khakpour et al. |
| 2017/0319292 | A1 | 11/2017 | Lifshitz et al. |

FOREIGN PATENT DOCUMENTS

| | | |
|---|---|---|
| GB | 2011305 | 7/1979 |
| IL | 219169 | 7/2012 |
| JP | 01-313048 | 12/1989 |
| JP | 2004-313659 | 11/2004 |
| JP | 2005-052754 | 3/2005 |
| JP | 2006-247619 | 9/2006 |
| JP | 2010-247133 | 11/2010 |
| WO | WO 00/45731 | 8/2000 |
| WO | WO 2009/137815 | 11/2009 |
| WO | WO 2011/060327 | 5/2011 |
| WO | WO 2012/069894 | 5/2012 |
| WO | WO 2013/157000 | 10/2013 |
| WO | WO 2015/059707 | 4/2015 |

OTHER PUBLICATIONS

Translation of Office Action and Search Report dated Oct. 10, 2015 From the State Intellectual Property Office of the People's Republic of China Re. Application No. 201380031375.8.
Supplementary European Search Report and the European Search Opinion dated Dec. 9, 2015 From the European Patent Office Re. Application No. 13778016.9.
International Preliminary Report on Patentability dated Oct. 30, 2014 From the International Bureau of WIPO Re. Application No. PCT/IL2013/050330.
International Search Report and the Written Opinion dated Mar. 19, 2015 From the International Searching Authority Re. Application No. PCT/IL2014/050924.
International Search Report and the Written Opinion dated Jul. 30, 2013 From the International Searching Authority Re. Application No. PCT/IL2013/050330.
Invitation to Pay Additional Fees dated Jan. 21, 2015 From the International Searching Authority Re. Application No. PCT/IL2014/050924.
Jiang et al. "Evaluation of A Sonic Device Designed to Activate Irrigant in the Root Canal", Journal of Endodontics, 36(1): 143-146, Jan. 2010.
Search Report and Written Opinion dated Mar. 4, 2015 From the Intellectual Property Office of Singapore Issued by the Austrian Patent Office Re. Application No. 11201406430V.
International Preliminary Report on Patentability dated May 6, 2016 From the International Bureau of WIPO Re. Application No. PCT/IL2014/050924.
Examination Report dated Sep. 4, 2015 From the New Zealand Intellectual Property Office Re. Application No. 701422.
Patent Examination Report dated Nov. 1, 2016 From the Australian Government, IP Australia Re. Application No. 2013250709. (3 pages).
Office Action dated Apr. 4, 2017 From the Israel Patent Office Re. Application No. 219169 and Its Translation Into English. (4 Pages).
Translation of Notice of Reasons for Rejection dated Feb. 21, 2017 From the Japan Patent Office Re. Application No. 2015-505069. (16 Pages).
Office Action dated Jul. 28, 2016 From the State Intellectual Property Office of the People's Republic of China Re. Application No. 201380031375.8 and Its Translation Into English.
Notification of the Request to Submit Additional Materials Dated Jun. 22, 2016 From the Eurasian Patent Organization, Eurasian Patent Office Re. Application No. 201491890 and Its Translation Into English.
Official Action dated Jul. 15, 2016 From the US Patent and Trademark Office Re. U.S. Appl. No. 14/522,250.
Notice of Reason for Rejection dated Feb. 21, 2017 From the Japan Patent Office Re. Application No. 2015-505069.
Invitation Pursuant to Rule 63(1) EPC Dated Apr. 20, 2017 From the European Patent Office Re. Application No. 14855775.4. (3 Pages).
Notice of Reasons for Rejection dated Sep. 12, 2017 From the Japan Patent Office Re. Application No. 2015-505069. (5 Pages).
Translation of Notice of Reasons for Rejection dated Sep. 12, 2017 From the Japan Patent Office Re. Application No. 2015-505069. (11 Pages).
Examination Report dated Jun. 16, 2017 From the Instituto Mexicano de la Propiedad Industrial Re. Application No. 2014/012423 and Its Translation Into English.
Examination Report dated Aug. 29, 2017 From the Australian Government, IP Australia Re. Application No. 2013250709. (4 Pages).

(56) References Cited

OTHER PUBLICATIONS

Supplementary Partial European Search Report and the European Search Opinion dated Aug. 11, 2017 From the European Patent Office Re. Application No. 14855775.4. (10 Pages).
Office Action dated Apr. 5, 2017 From the State Intellectual Property Office of the People's Republic of China Re. Application No. 201380031375.8 and Its Summary Into English. (7 Pages).
Communication Pursuant to Article 94(3) EPC Dated Jun. 22, 2017 From the European Patent Office Re. Application No. 13778016.9. (6 Pages).
Translation Dated May 24, 2017 of Office Action dated Apr. 5, 2017 From the State Intellectual Property Office of the People's Republic of China Re. Application No. 201380031375.8. (3 Pages).
Notification of the Request to Submit Additional Materials dated Feb. 18, 2018 From the Eurasian Patent Organization, Eurasian Patent Office Re. Application No. 201491890 and Its Translation Into English. (8 Pages).
Notice of Reasons for Rejection dated Jul. 24, 2018 From the Japan Patent Office Re. Application No. 2016-525911 and Its Translation Into English.
Communication Pursuant to Article 94(3) EPC Dated Jun. 26, 2018 From the European Patent Office Re. Application No. 14855775.4. (4 pages).
Examination Report dated Jun. 16, 2018 From the Australian Government, IP Australia Re. Application No. 2014338513. (6 Pages).
Notice of Reasons for Rejection dated Jun. 26, 2018 From the Japan Patent Office Re. Application No. 2015-505069 and Its Translation Into English. (5 Pages).
Examination Report dated Feb. 20, 2018 From the Instituto Mexicano de la Propiedad Industrial, IMPI, Direccion Divisional de Patentes Re. Application No. MX/a/2014/012423 and Its Translation Into English. (12 Pages).
Translation of Notification of Office Action dated Jan. 12, 2018 From the State Intellectual Property Office of the People's Republic of China Re. Application No. 201480070236.0. (11 Pages).
Requisition by the Examiner dated Jan. 7, 2019 From the innovation, Science and Economic Development Canada, Canadian Intellectual Property Office Re. Application No. 2,869,836. (4 Pages).
Examination Report Notification dated Feb. 21, 2019(*) from the Instituto Mexicano de la Propiedad Industrial, Direccion Divisional de Patentes Re. Application No. MX/a/2014/012423 and its Translation into English (*dated Oct. 25, 2018). (13 Pages).
Notice of Reason for Rejection dated Mar. 5, 2019 From the Japan Patent Office Re. Application No. 2016-525911 and Its Translation Into English. (17 Pages).

\* cited by examiner

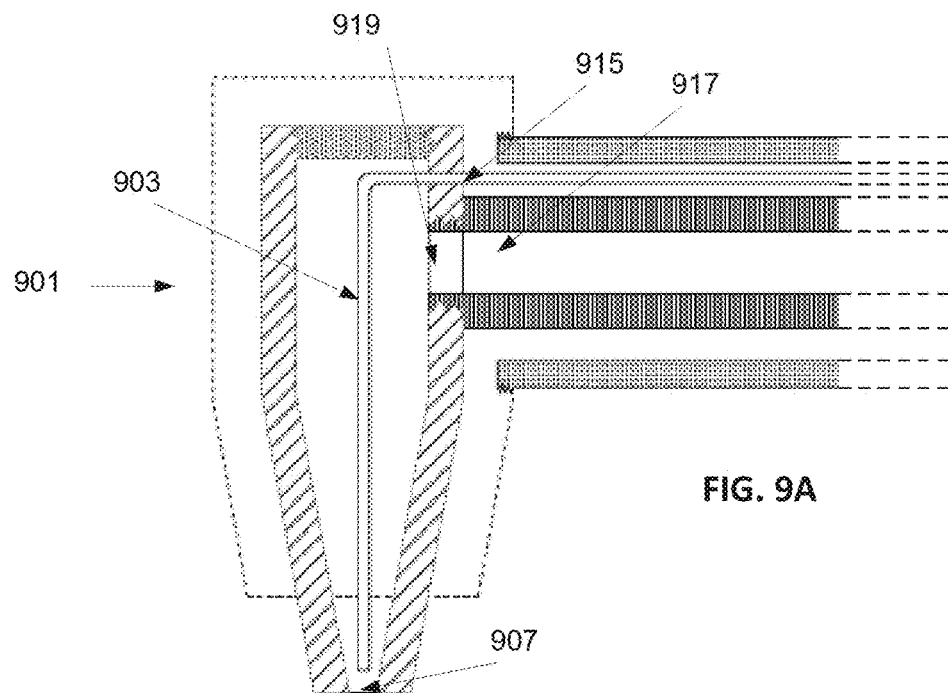
FIG. 9A
FIG. 9B
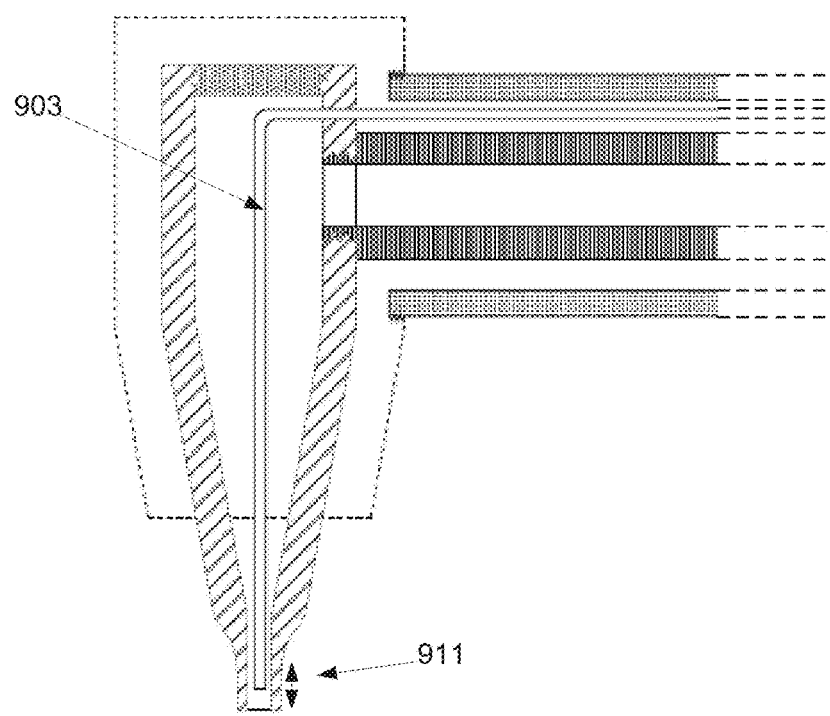

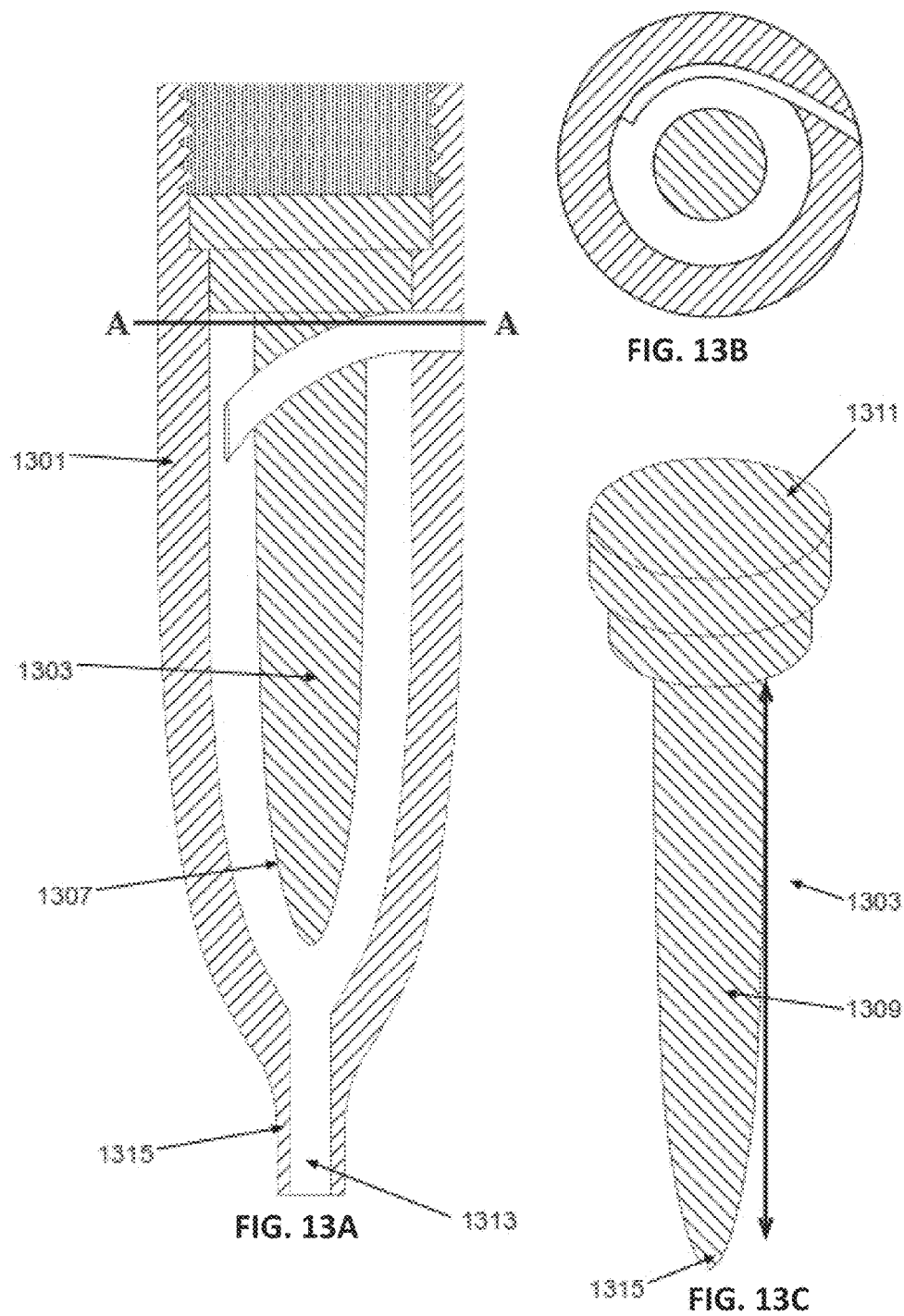

FEASIBILITY STUDY FOR: APPARATUS AND METHOD FOR ENDODONTIC TREATMENT

STUDY PURPOSE: feasibility test for novel apparatus and endodontic treatment                                             Date: 28/02/13

The process supported with "Before and After" evidence results which supported with CT Imaging, Axial Mode for evaluate the thickness of the eroding layer in the root canal. Using Electro scan microscope (X 5000 magnification) testing the cleanliness of the root canal.

| Tooth Nr. | Total of canals per each specim. | Root Canal Type ||||| Duration of Treatment in Seconds ||| Apex Pene- Tration | sidelong penetration by canal with a thin Wall | Average Eroding layer in microns | Comments |
|---|---|---|---|---|---|---|---|---|---|---|---|---|---|
| | | Stand. Canal (X) | Curve Canal (X) | Sharp Curved Canal (X) | Canal with Open Apex (X) | Extremely narrow canal (X) | 15 (X) | 30 (X) | 45 (X) | (Yes/No) | (Yes/No) | | |
| 1 | 2 | 1 | 1 | | 4 | | | x | | N | N | 100-200 | Apex was open initially; cleaning might have caused a slight widening of the opening |
| 2 | 4 | 1 | 2 | 1 | | | x | | | N | N | 100-200 | Hole accidently created on the side during the tooth opening |
| 3 | 3 | 1 | 1 | 1 | | 2 | | x | | N | N | 100-200 | |
| 4 | 4 | 2 | | 2 | 3 | 1 | | | x | N | N | 100-200 | Apex was open initially; cleaning might have caused a slight widening of the openings |
| 5 | 3 | 1 | 1 | 1 | | 2 | | | x | N | N | 100-200 | |
| 6 | 3 | | 2 | 1 | | | | x | | N | N | 100-200 | |
| 7 | 3 | 2 | 1 | | | | | | x | N | N | 100-200 | |
| 8 | 4 | 2 | 2 | 2 | | | | | x | N | N | 100-200 | |
| 9 | 3 | | 1 | | 1 | 2 | x | | | N | N | 100-200 | Apex was open initially; cleaning might have caused a slight widening of the opening |
| 10 | 3 | 2 | | 1 | 3 | | | | | N | N | 100-200 | Apex was open initially; cleaning might have caused a slight widening of the opening |

FIG. 16A

| Tooth Nr. | Root Canal type | | | | | | Duration of Treatment in Seconds | | | Apex Penetration | sidelong penetration by canal with a thin Wall | Average Eroding layer in microns | Comments |
|---|---|---|---|---|---|---|---|---|---|---|---|---|---|
| | Total of canal per each specim. | Stand. Canal (X) | Curve Canal (X) | Sharp Curved Canal (X) | Canal with Open Apex (X) | Extremely narrow canal (X) | 15 (X) | 30 (X) | 45 (X) | (Yes/No) | (Yes/No) | | |
| 11 | 3 | 1 | | 2 | 1 | 2 | | | | N | N | 100-200 | |
| 12 | 4 | 2 | 1 | 1 | 3 | 2 | | x | x | N | N | 100-200 | Apex was open initially; cleaning might have caused a slight widening of the opening |
| 13 | 3 | 3 | | | 1 | | | x | | N | N | 100-200 | Apex was open initially; cleaning might have caused a slight widening of the opening |
| 14 | 4 | 1 | 2 | 1 | | | | | x | N | N | 100-200 | Hole accidently created on the bottom between canal, during the tooth opening |
| 15 | 3 | 2 | 1 | 1 | 1 | 1 | | x | | N | N | 100-200 | Apex was open initially; cleaning might have caused a slight widening of the opening |
| 16 | 4 | 1 | 1 | 2 | | | x | | | N | N | 100-200 | 1 canal was broken before the cleaning procedure |
| 17 | 4 | 3 | | 1 | | | x | | | N | N | 100-200 | |
| 18 | 3 | 1 | | 2 | 3 | | x | | | N | N | 100-200 | Apex was open initially; cleaning might have caused a slight widening of the opening |
| 19 | 2 | 1 | 1 | | | | | | x | N | N | 100-200 | |
| 20 | 1 | 1 | | | | | | x | | N | N | 100-200 | |

FIG. 16A (continued)

| Tooth Nr. | Total of canal per each specim. | Root Canal type | | | | | Duration of Treatment in Seconds | | | Apex Penetration | sidelong penetration by canal with a thin Wall | Average Eroding layer in microns | Comments |
|---|---|---|---|---|---|---|---|---|---|---|---|---|---|
| | | Stand. Canal (X) | Curve Canal (X) | Sharp Curved Canal (X) | Canal with Open Apex (X) | Extremely narrow canal (X) | 15 (X) | 30 (X) | 45 (X) | (Yes/No) | (Yes/No) | | |
| 21 | 1 | 1 | | | | | x | | | N | N | | |
| 22 | 3 | 1 | 2 | | | | x | | | N | N | 100-200 | |
| 23 | 3 | 1 | | 2 | 2 | | x | | | N | N | 100-200 | Apex was open initially, cleaning might have caused a slight widening of the opening |
| 24 | 4 | 3 | 1 | | 3 | | x | | | N | N | 100-200 | Apex was open initially, cleaning might have caused a slight widening of the opening |
| 25 | 3 | | 2 | 1 | 1 | | x | | | N | N | 100-200 | Apex was open initially, cleaning might have caused a slight widening of the opening |
| 26 | 3 | 1 | | 2 | | | | x | | N | N | 100-200 | Apex was broken and open initially - (M) size for 3 canals |
| 27 | 3 | 1 | 2 | | | | | x | | N | N | 100-200 | |
| 28 | 4 | 2 | 1 | 1 | 2 | 2 | | | x | N | N | 100-200 | Apex was open initially, cleaning might have caused a slight widening of the opening |
| 29 | 2 | 1 | 1 | | 1 | | | x | | N | N | 100-200 | Apex was open initially, cleaning might have caused a slight widening of the opening |
| 30 | 3 | 2 | 1 | | 1 | 1 | | | x | N | N | 100-200 | Apex was open initially, cleaning might have caused a slight widening of the opening |

FIG. 16B

| Tooth Nr. | Total of canal per each specim. | Root Canal type Tooth No ||||| Duration of Treatment in Seconds ||| Apex Penetration | sidelong penetration by canal with a thin Wall | Average Eroding layer in microns | Comments |
|---|---|---|---|---|---|---|---|---|---|---|---|---|---|
| | | Stand. Root Canal (X) | Curve Canal (X) | Sharp Curved Canal (X) | Canal with Open Apex (X) | Extremely narrow canal (X) | 15 (X) | 30 (X) | 45 (X) | (Yes/No) | Yes/No | | |
| 31 | 4 | 1 | 2 | 1 | | 3 | | x | | N | N | 100-200 | |
| 32 | 4 | | 2 | 2 | | | | | x | N | N | 100-200 | |
| 33 | 4 | 2 | 1 | 1 | 2 | 1 | x | | | N | N | 100-200 | Apex was open initially; cleaning might have caused a slight widening of the opening |
| 34 | 3 | 1 | 2 | | | | | x | | N | N | 100-200 | |
| 35 | 3 | | 2 | 1 | | | x | | | N | N | 100-200 | |
| 36 | 3 | 1 | 1 | 1 | | 2 | | | x | N | N | 100-200 | |
| 37 | 3 | 2 | 1 | | | | | x | | N | N | 100-200 | Apex was open initially; cleaning might have caused a slight widening of the opening |
| 38 | 4 | 1 | 2 | 1 | 1 | 2 | | x | | N | N | 100-200 | Apex was open initially; cleaning might have caused a slight widening of the opening |
| 39 | 3 | 3 | | | | | | | x | N | N | 100-200 | |
| 40 | 1 | 1 | | | | 1 | | | x | N | N | 100-200 | |
| 41 | 1 | 1 | | | | | | x | | N | N | 100-200 | |

FIG. 16B (continued)

APPARATUS AND METHOD FOR ENDODONTIC TREATMENT

RELATED APPLICATIONS

This application is a National Phase of PCT Patent Application No. PCT/IL2013/050330 having International filing date of Apr. 15, 2013, which claims the benefit of priority of Israel Patent Application No. 219169 filed on April 15, 2012. The contents of the above applications are all incorporated by reference as if fully set forth herein in their entirety.

FIELD AND BACKGROUND OF THE INVENTION

The present invention, in some embodiments thereof, relates to an apparatus and method for endodontic treatment and, more particularly, but not exclusively, to an apparatus and method for treating a root canal using one or more angled fluid jets.

In cases where a tooth is decayed, infected, or abscessed, a root canal procedure may be performed to eliminate infection and decontaminate the tooth. During the root canal procedure, substances such as nerve and pulp tissue are removed in order to prevent future infection.

Current methods for treating a root canal may involve the use of files, such as metal files, for removing tissue such as nerve tissue, magma, pulp tissue or blood vessels from the root canal. In some cases, a rotary file drill is used for shaping a root canal and optionally widening a portion of it to enable access. One of the risks of the use of files for endodontic treatment is the spreading of a smear layer, which may include organic and/or inorganic debris, on the root canal wall after instrumentation. Another potential risk of the use of files may include wounding of the root canal wall or apex.

Endodontic treatment devices have been disclosed by several publications.

U.S Patent Publication Number 6224378 to Valdes et al. discloses "A method and apparatus for dental procedures using a dental hydrojet tool having a cannula extending therefrom. The cannula is connected to a source of high pressure liquid, and delivers a high velocity, high pressure jet. For root canal procedures, the cannula is directed through an opening formed in the crown of the tooth, and the hydrojet is directed at the pulp, nerve and vascular tissue within the interior chamber."

U.S Patent Publication Number 4021921 to Detaille discloses "a device for treating the pulp canals and -chamber of a tooth, the crown of which presents a previously opened pulp-chamber in which said canals open, comprising an apparatus tightly adaptable to the crown of the tooth and providing in the pulp-chamber and the pulp-canals of said tooth for the circulation of a treating solution acting substantially upon the vasculo-nervous bundle or the necrotic-magma of the tooth; the pressure of the treating solution being subjected within the pulp-chamber and the pulp-canals to periodical impulses combined to oscillations of substantially higher frequency."

SUMMARY OF THE INVENTION

The present invention, in some embodiments thereof, relates to an apparatus and method for endodontic treatment and, more particularly, but not exclusively, to an apparatus and method for treating a root canal using one or more angled fluid jets.

According to an aspect of some embodiments of the present invention there is provided an apparatus and method for endodontic treatment.

According to an aspect of some embodiments of the present invention there is provided an apparatus for endodontic treatment comprising a nozzle, the nozzle comprising a tip small enough to be inserted through a pulp chamber of a tooth, the nozzle is shaped to create a beam comprising at least one fluid jet in an angle to a vertical axis of the nozzle, so that it flows along a wall of a root canal to remove soft tissue, and the nozzle is connected to an input pipeline. According to some embodiments, the nozzle comprises an internal cone and an external cone defining a lumen between them for the fluid to flow through. According to some embodiments, the nozzle comprises a tube extending between a lumen of the internal cone and the lumen between the internal cone and the external cone. According to some embodiments, the fluid circulates in a helical flow through the lumen for exiting the nozzle in an angle. According to some embodiments, the angled fluid jet does not intersect a vertical axis of the nozzle. According to some embodiments, the nozzle comprises channels for creating at least one angled jet. According to some embodiments, there is provided a system comprising: the apparatus, a liquid tank, and an air compressor, wherein the input pipeline of the apparatus passes through a handle to connect the liquid tank and/or air compressor to the nozzle. According to some embodiments, the system is electrically controlled by using a control panel an electric circuit. According to some embodiments, the fluid comprises gas and/or liquid and/or abrasive powder. According to some embodiments, the gas is air, and the fluid comprises between 50-95% air, and between 5-50% liquid. According to some embodiments, the nozzle is shaped so that the fluid exits the nozzle as an aerosol. According to some embodiments, the apparatus is connected to an air compressor with a pressure ranging between 5-200 PSI. According to some embodiments, the apparatus is connected to a fluid tank which provides fluid at a volumetric flow rate ranging between 0.1-50 ml/sec. According to some embodiments, the angled jet has tangential and vertical velocity components in respect to the root canal wall. According to some embodiments, the apparatus comprises a suction cone for collecting returning fluid and debris, and the suction cone has a tip sized to fit within a pulp chamber of a tooth.

According to an aspect of some embodiments of the present invention there is provided a method for endodontic treatment comprising directing at least one fluid jet at an angle which causes it to flow along a wall of a root canal so that the flow removes material from the root canal wall. According to some embodiments, removing comprises separating soft tissue from the root canal wall. According to some embodiments, the flow comprises a helical flow along the root canal wall. According to some embodiments, the root canal comprises at least one narrowing portion, and the flow comprises flowing through the narrowing portion along the wall of the root canal. According to some embodiments, the root canal comprises a curvature and/or a branching, and the flow comprises flowing through the curvature and/or the branching. According to some embodiments, the method comprises positioning a nozzle above an entrance to the root canal so that at least one angle fluid jet hits a wall of the root canal. According to some embodiments, fluid flows along the wall of at least a portion of the root canal so that the fluid returns upwards along at least a portion of a central lumen of the root canal. According to some embodiments, the method comprises eroding a layer of dentin tissue from at least a portion of the root canal wall. According to some embodiments, the layer has thickness ranging between 100-200 μm. According to some embodiments, the angled jet is created by circulating the fluid in a helical flow within a nozzle of an apparatus. According to some embodiments, the soft tissue comprises nerve tissue, and/or pulp tissue and/or blood vessels. According to some embodiments, the method does not leave a smear layer on the root canal wall. According to some embodiments, directing comprises directing the fluid jets in pulses. According to some embodiments, directing includes clearing a root canal to prepare for sealing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings:

FIGS. 9A-9D are illustrations of a conical nozzle comprising a pipe extending between a handle and an exit aperture of the nozzle, according some embodiments of the invention;

FIGS. 13A-13D are illustrations of a nozzle comprising a cone and a pin shaped element occupying at least a portion of the internal lumen of the cone, according to some embodiments of the invention;

FIGS. 16A-B is a table of experimental results of an experiment for testing the feasibility of an apparatus for endodontic treatment, according to some embodiments of the invention.

DESCRIPTION OF SPECIFIC EMBODIMENTS OF THE INVENTION

Figure 1:
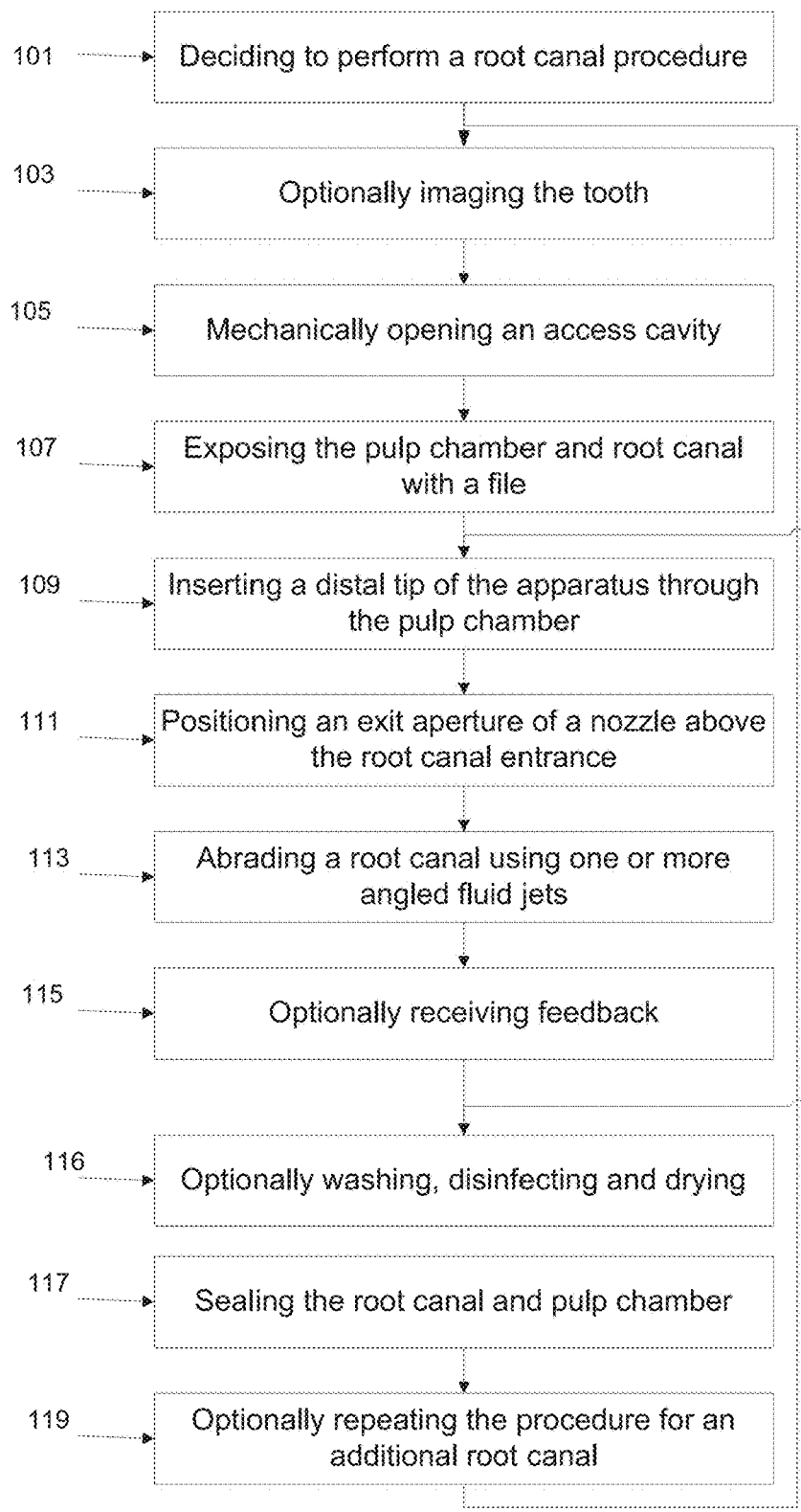
FIG. 1 is a flowchart of an exemplary endodontic treatment procedure, according to some embodiments of the invention.

The present invention, in some embodiments thereof, relates to an apparatus and method for endodontic treatment and, more particularly, but not exclusively, to an apparatus and method for treating a root canal using one or more angled fluid jets.

In some embodiments, the apparatus is used for cleaning, abrading, and/or decontaminating a root canal of a tooth before sealing the tooth.

An aspect of some embodiments of the invention relates to cleaning and/or abrading a root canal using one or more angled fluid jets. In some embodiments, once the angled jet hits the root canal wall, the force exerted by the wall channels the jet to travel down the root along the wall. In some embodiments, the angle includes a component outside the plane of the axis of root canal, so that the flow spins in a helical flow along some or all the root canal. In some embodiments, the fluid advances along the root canal wall to remove organic substance and/or abrade the canal wall. In some embodiments, the angled fluid jet does not cross a vertical axis of the root canal and/or a vertical axis of the nozzle.

In some embodiments, the passing of the flow through the canal is facilitated by the fluid advancing along the wall. In some embodiments, the flow of fluid passes through a narrowing portion of the root canal to clean and/or abrade the narrowing and/or distal section of the root canal. In some embodiments, the flow of fluid continues to the apex of the root canal. In some embodiments, at least some of the fluid flows back up through the root canal, washing away soft tissue such as nerve tissue, blood vessels, magma and/or debris. In some embodiments, since the flow of fluid advances along the canal wall, the returning fluid passes upwards through the center of the canal. Optionally, the resulting flow path allows continual irrigation for cleaning and/or abrading the root canal. Optionally, irrigation is performed periodically to allow fluid to exit the canal. In some embodiments, a volumetric flow rate of fluid that passes through the root canal ranges between 0.5-50 ml/second, for example between 1-9 ml/second, 30-40 ml/second.

In an exemplary embodiment of the invention, the flow travels along the wall of the root canal for at least 20%, 50%, 70%, 90% or intermediate or greater percentages of the length of the root canal. In some cases, part of the flow, for example, at the distal end of the canal, includes a significant turbulent flow (e.g., away and towards the wall).

In some embodiments, the direction and/or magnitude of the momentum of the fluid exiting a nozzle of the apparatus is determined by the structure of the nozzle. In an exemplary embodiment, the fluid is circulated in a lumen formed between two cones within the nozzle so that it exits the nozzle in an angle to a vertical axis of the nozzle. In another embodiment, passing the fluid within a structural element of the nozzle, such as an inclined tube configured on a plane that crosses the vertical plane of the tooth may create the angled direction of the jets.

An aspect of some embodiments of the invention relates to a fast flow of fluid that passes through the root canal and optionally enters at least a portion of the dentinal tubules. In some embodiments, a ratio between gas (such as air) and liquid (such as water, disinfectant, antiseptic medication, and/or any other solution) is used. In one example, a fluid may comprise 90% air and 10% liquid. In some embodiments, the selected ratio may affect parameters such as the elasticity of the fluid, the velocity of the fluid, and/or the flow rate. Optionally, components of the fluid such as air bubbles may facilitate the removal of organic substance from the canal wall.

In some embodiments, a relatively low source pressure of the jet or a beam of jets exiting a nozzle is used, for example ranging between 10-200 PSI. In some embodiments, the pressure of the angled jet when hitting a wall of the root canal is lower, for example ranging between 5-150 PSI.

In some embodiments, the fast flow of fluid erodes a layer of tissue, for example dentin tissue. Optionally, eroding is accomplished by adding abrasive particles to the fluid, which are then pushed against the walls of the canal, sweeping away a layer of dentinal tissue, magma, debris and/or bacteria. In some embodiments, eroding of at least 50-80%, 20-30%, 80-90% of a surface of the root canal wall is performed. In some embodiments, the flow of fluid smoothes the root canal wall.

In some embodiments, the root canal wall is subjected to shear forces exerted by the flow of fluid. Optionally, a thin layer of tissue is removed due to the applied force. In some embodiments, turbulent flow may be observed in at least a portion of the root canal, for example in proximity to the apex. Optionally, a turbulent flow may increase the shear forces exerted by the flow of fluid.

In some embodiments, various parameters of the apparatus and/or system such as the angle of the fluid jet, the ratio between gas and liquid, the type of abrasive powder and/or any other parameters or combinations of them may be selected to optimize the effectiveness of the apparatus and/or system.

In an exemplary embodiment of the invention, a plurality of jets are used. Optionally, the use of a plurality of jets allows more freedom (e.g. less manual precision and/or allowing matching to various geometries) in the orientation of the nozzle, as it is more likely that at least one jet will have an angle needed for proper treating of the root canal. Optionally or alternatively, the use of multiple jets may assist in ensuring that all of the root canal wall is hit by fluid flow at sufficient velocity and/or other parameters.

In some embodiments, the jets will be contiguous with each other, for example, in the form of a cone and/or a segment thereof.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a flowchart of an endodontic treatment procedure, in accordance with an exemplary embodiment of the invention.

In some cases, for example if a tooth is decayed, infected, and/or cracked, a dentist may decide to perform a root canal procedure, as described at 101.

Commonly, the number of root canals in a tooth depends on the number of the tooth roots, for example ranging between 1-5.

In some embodiments, a root canal procedure includes removing pulp tissue (pulpectomy), magma, nerve tissue, and/or blood vessels from the pulp chamber and root canal to prevent future infection and/or an abscessed tooth. In some embodiments, the root canal procedure includes shaping the root canal. In some embodiments, the root canal procedure includes decontaminating the tooth. A feature of some embodiments includes not performing one or more of the above, for example not performing shaping of the root canal.

In an exemplary embodiment of the invention, for example, as will be described below, the root canal is cleaned without leaving a smear layer which, for example, would otherwise block tubules and/or serve as a substrate for infection.

Prior to and/or during the procedure, imaging of the tooth may be performed, as described at 103. For example, X-ray imaging may be performed to determine the shape (or number) of the root canals and/or detect signs of infection.

At 105, an access cavity to the pulp chamber and root canal is created through the crown of the tooth, for example using a dental drill. Once the access cavity is created, the entrance to the root canal is exposed, as described at 107, optionally using a root canal file inserted through the access cavity into the pulp chamber. In some embodiments, access is provided via a side of the tooth. This may be possible if no files are used on the root canal, for example, as described below.

At this stage, in order to clean, shape and/or decontaminate the root canal through the exposed entrance, a distal tip of the apparatus, optionally including a nozzle as will be further described, is inserted through the pulp chamber, as described at 109, and an exit aperture of the nozzle is positioned above the exposed entrance to the root canal, as described at 111. Optionally, the exit aperture of the nozzle is positioned within the root canal, as will be further described. Optionally, the exit aperture of the nozzle is positioned in an angle to the root canal entrance. At 113, one or more angled fluid jets discharged from the exit aperture of the nozzle passes through the root canal, as will be explained by the following figure. In some embodiments, as the flow of fluid advances along the root canal wall, it removes tissue. In some embodiments, the flow of fluid removes organic substance such as pulp tissue, nerve tissue, blood vessels, magma and/or debris from the root canal. In some embodiments, the flow of fluid erodes a thin layer of dentin tissue from the wall of a root canal. In some embodiments, the flow of fluid smoothes the root canal wall. In some embodiments, the flow of fluid disinfects the root canal.

In some cases, manual cleaning (e.g. using a file or other methods known in the art) is used to remove some or all bulk debris from a canal before using fluid jets as described herein. Optionally, fluid jets are used to remove a smear layer created by manual cleaning.

At 115, the dentist may optionally evaluate the effectiveness of the cleaning and/or abrading procedure, for example by inserting a file to reach the apex of the root canal and test for remains of infected tissue. Optionally, a dentist may re-wash and/or dry and/or disinfect the root canal (116).

At this stage, sealing of the root canal (and/or the pulp chamber) is optionally performed (117). Optionally, sealing includes filling a hollow interior of the root canal. In some embodiments, a rubber compound such as Gutta Percha material may be used for sealing the root canal. Optionally, the Gutta Percha material is softened and injected into the root canal, in which it then hardens. Alternatively, a more solid form of Gutta Percha, for example shaped as a cone, is inserted into the root canal to fill it. In some embodiments, the sealing process begins by inserting the filling material to the apex of the root canal, and then advancing upwards. In some embodiments, a temporary filling is used, which is later replaced by a permanent filling.

In various acts described above, techniques that are known in the art may be used. The acts described at 109-113 desirably use an embodiment of an inventive apparatus and method for cleaning and/or abrading a root canal, for example, as described below.

Optionally, the procedure described at 101-117 is repeated for one or more additional root canals, for example an additional root canal of the same tooth and/or a root canal of a different tooth. Optionally, sealing is performed for the one or more root canals that were treated.

Figure 2:
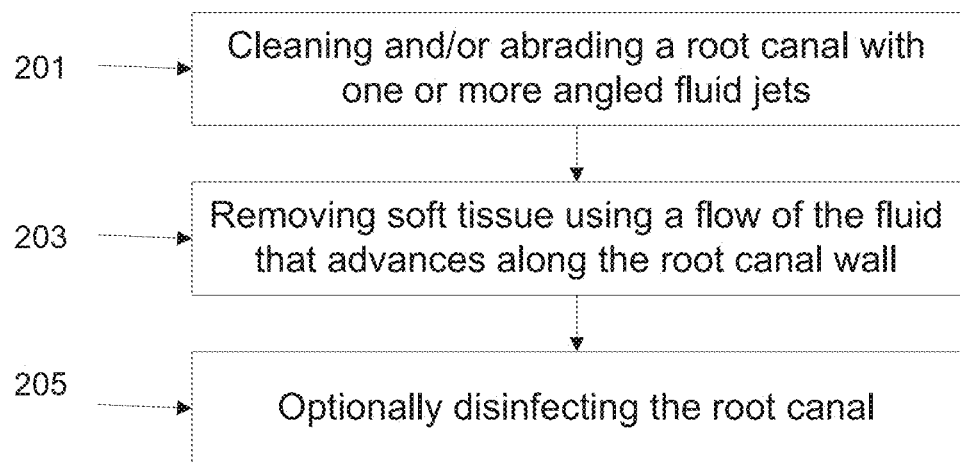
FIG. 2 is a flowchart of an exemplary method for cleaning and/or abrading a root canal using one or more angled fluid jets, according to some embodiments of the invention.

FIG. 2 is a flowchart of an exemplary method for cleaning and/or abrading a root canal using one or more angled fluid jets, according to some embodiments of the invention.

At 201, one or more angled fluid jets are directed into a root canal to clean and/or abrade it.

In some embodiments, a jet is a directed flow of fluid, optionally exiting from an exit aperture of a nozzle. Different embodiments may have jets with different shapes and/or forms. For example, the jet may have a narrow ray form. In some embodiments, a beam of a plurality of jets is used. In some cases, the jet is thin and flat and may spread out angularly. In other embodiments, a jet is substantially pencil like, but spreads when contacting the root canal wall. In an exemplary embodiment of the invention, the jet shape is a property of the nozzle used. In some embodiments, the shape of the jet may depend on the fluid parameters, such as air/liquid ration and/or pressure and/or pulsatility. In other embodiments, the nozzle may be able to selectively provide one of several jet forms.

In some embodiments, each of a plurality of angled jet has hits the root canal wall at a different angle so that the plurality of jets are channeled to flow together along the root canal wall in a helical pattern, as will be further described.

In some embodiments, the one or more jets are directed into the root canal. In some embodiments, at least a portion of a single jet or a plurality of jets hits the wall of the root canal. In some embodiments, force exerted by the wall channels the jets to advance along the root canal wall. In some embodiments, the fluid flows in a helical flow pattern along the walls of the root canal, for example, as will be further described in the following figure.

In some embodiments, as will be further explained, the one or more jets are discharged from a nozzle such that they are angled to a vertical axis of the nozzle. In some embodiments, the one or more jets enter the root canal such that they are angled to a vertical axis of the root canal. Optionally, the vertical axis of the nozzle unites with the vertical axis of the root canal.

In some embodiments, the shunting of the one or more jets in a specific angle and/or direction is created by a designated inner structure of the nozzle, for example, as will be further explained below.

In some embodiments, a plurality of angled jets such as 2, 4, 8, 12, 50, 1000, or any intermediate or higher numbers are used. A potential advantage of using a plurality of jets may include homogenous cleaning and/or eroding of the canal wall. Another potential advantage of using a plurality of jets includes the ability to select a hitting angle, for example an angle of 30°, 45°, 70° between the angled jet and the root canal wall, and additionally and/or alternatively to assure that at least some of the jets of the beam will hit the root canal wall.

In some embodiments, a single angled jet may be used, for example being narrow enough to effectively advance along the canal wall, creating a thin coating-like layer of fluid. Optionally, in the above described phenomena, the angled jets advance along the canal wall, optionally allowing some or all of the returning fluid to flow back up through a central lumen along the vertical axis of the canal, as will be shown by the following figure. For example, 60-80%, 40-50%, 80-95% of the fluid may flow back through the central lumen, and 10-30%, 5-8%, 30-40%, may flow back up along the canal wall.

In some embodiments, as described at 203, the flow of fluid passing through the root canal removes soft tissue such as pulp tissue, magma, nerve tissue, and/or blood vessels. In some cases, the tissue removed is infected tissue. In some embodiments, the flow of fluid flushes away organic substance and/or debris.

In some embodiments, the flow of fluid erodes a layer of tissue, for example a thin layer, such as a thin layer of dentin tissue. Optionally, the flow of fluid causes widening of the canal. In some embodiment, the flow of fluid smoothes the surface of the root canal wall. For example, the thickness of the eroded layer may range between 100-200 μm, 10-70 μm, 200-300 μm. Optionally, the thickness of the eroded layer and/or the amount of debris removed by the flow depends on various parameters, such as the application time.

In some embodiments, the fluid comprises liquid, such as water and/or antibacterial liquid. Additionally and/or alternatively, the fluid comprises gas, such as air. Optionally, the mixture of air and liquid dispersed from the nozzle is an aerosol. Optionally, the pressure of the aerosol exiting a nozzle ranges between 10-200 PSI.

In some embodiments, a ratio between air and liquid is selected according to the need, for example a ratio between air and liquid may affect the velocity of the fluid flowing through the canal. In an exemplary embodiment, the fluid comprises between 60-90% air, and between 10-40% liquid. In another example, the ration between air and liquid is 90% liquid, and 10% air. In another example, the fluid comprises 100% liquid.

In some embodiments, eroding of the tissue is achieved by adding abrasive particles such as an abrasive powder to the fluid. Optionally, the abrasive powder comprises between 0.01-3%, 2-2.5%, 0.8-1.2% of the fluid. Some examples of abrasive powder that may be added to the mixture of air and liquid include crystallite, silicon powder, garnet powder, aluminum powder, magnesium powder, ceramic powder, plastic powder, synthetic, emery powders, sea shell powder, cement powder, salt, ground seeds and/or combinations of the above. In some embodiments, the powder grains may have a diameter ranging between 2-500 µm, 10-50 µm, 3-6 µm. In some embodiments, the powder grains may be selected according to the type of tissue that is to be removed. In some embodiments, air bubbles can act as an abrasive substance, for example to erode tis sue.

In some embodiments, the flow of fluid disinfects the root canal, as described at 205, for example by adding disinfectant to the fluid. Optionally, an antibacterial substance and/or medicine is added. In one example, Sodium Hypochlorite is added to the fluid to be passed through the root canal, optionally followed by saline and hydrogen peroxide, to disinfect the root canal. In some embodiments, there are three fluid sources that can be used such as water, disinfectant, and medicine. Optionally, the fluid comprises one or more of these liquids.

In some embodiments, the duration of the process of removing organic substance, eroding the tissue and/or disinfecting the interior of the root canal ranges between 15-45 seconds, for example 20 seconds, 27 seconds, 43 seconds. In some embodiments, for example if the root canal has an extremely narrow portion, the duration of the above process may range between 45-60 seconds, for example 50 seconds, 55 seconds. Optionally, shorter, intermediate and/or longer time periods are required to complete the process. In some embodiments, the treatment is provided in periodic pulses, for example a 10 second duration followed by a 10 second interval, or a 2 second duration followed by a 5 second interval, or any other combination. In some embodiments, during the interval access fluid is collected from the root canal, for example by suctioning.

Figure 3:
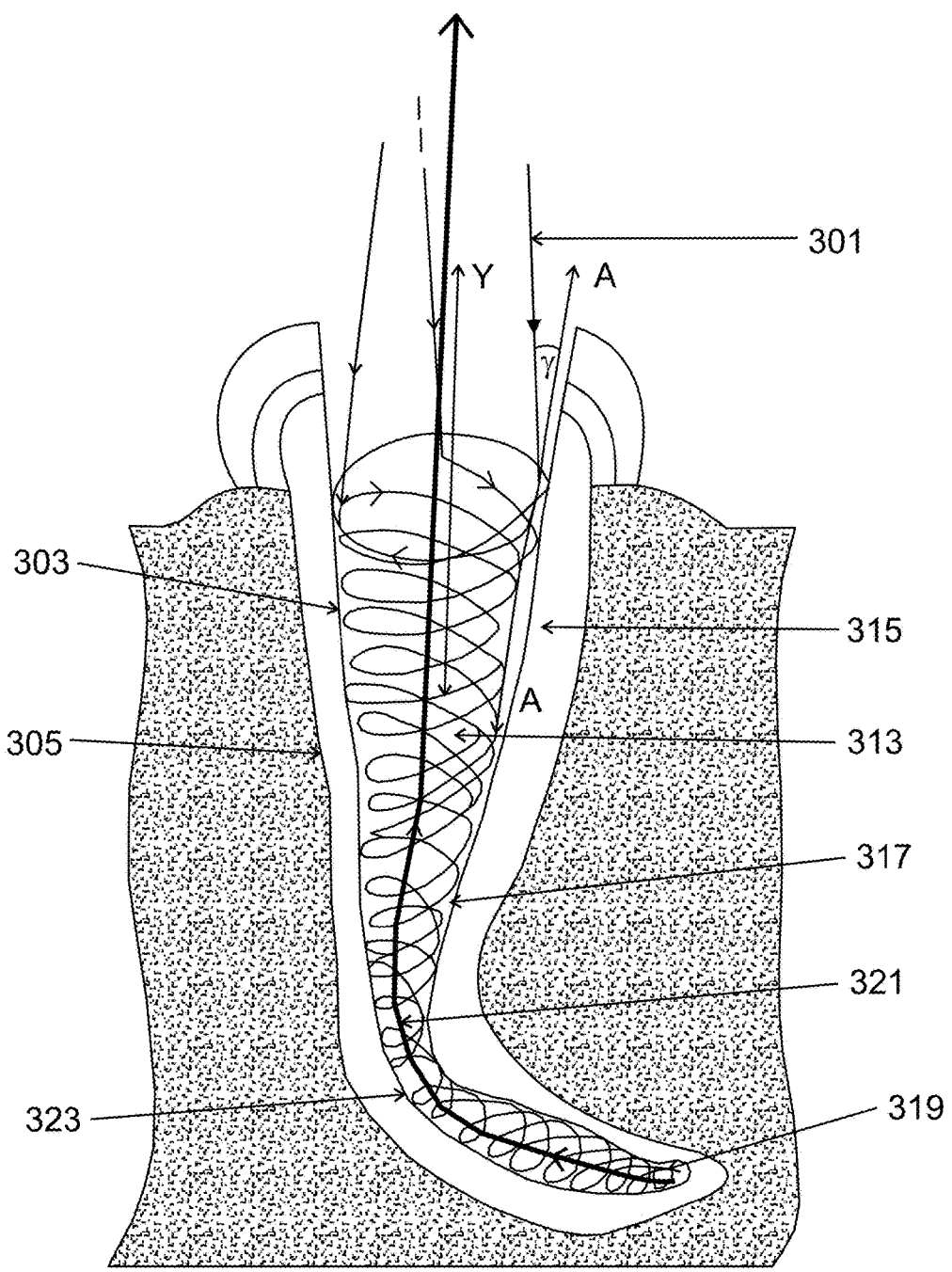
FIG. 3 is an illustration of angled fluid jets entering a root canal and advancing along the root canal wall in a helical flow, according to some embodiments of the invention.

FIG. 3 shows angled fluid jets entering a root canal and advancing along the root canal wall in a helical flow, according to some embodiments of the invention.

In some embodiments, angled fluid jet 301 hits wall 303 of the root canal 305. In some embodiments, the plane in which the angled fluid jet passes before and/or during entrance to the root crosses a vertical plane of the tooth, for example a plane in which vertical axis y passes, as will be explained.

In some embodiments, an angle γ is formed between jet 301 and an axis extending longitudinally along the canal wall 303, such as axis AA. In some embodiments, for example if a portion of the root canal is shaped as a cylinder, axis AA may be parallel to vertical axis y. In some embodiments, angle γ is an acute angle, for example ranging between 10-85 degrees, for example 20 degrees, 45 degrees, 73 degrees. In some embodiments, angle γ is zero.

In some embodiments, one angled jet 301 or a plurality of angled jets hit the root canal wall. In some embodiments, the jets advance along the root canal wall. In some embodiments, once the jets hit the root canal wall, the force exerted by the wall channels the jets to spin in a helical flow 313 through the root canal. Optionally, other forms of flow such as longitudinal stream lines along the root canal wall are formed.

In some embodiments, flow 313 advances along a portion 315 of the root canal. In some embodiments, portion 315 is cylindrical. In some embodiments, flow 313 passes through a narrowing portion 317 of the root canal. In some embodiments, flow 313 passes through a narrowing portion and then through a widening portion. In some embodiments, flow 313 passes through a curve 323.

In some embodiments, narrowing portion 317 includes a portion having a diameter less than 0.1 mm, less than 0.05 mm, and/or intermediate or smaller values. In some embodiments, curve 323 has a radius of curvature less than 0.05 mm, less than 0.08 mm, and/or intermediate or smaller numbers. In some embodiments, a length of a root canal past curvature and/or past a narrowing which the fluid flows through ranges, for example, between 0.1-4 mm, for example 1 mm, 0.5 mm, 2 mm.

In some embodiments, flow 313 reaches apex 319 of the root canal. In some embodiments, flow 313 passes through branches of the root canal, for example reaching at least a portion of branching dentinal tubules, (not shown in this figure). In some embodiments, for example if the anatomy of root canal 305 is unusual, such as an L-shaped or C-shaped root canal, and/or if root canal 305 has an extremely narrowing portion, flow 313 may pass through and clean at least most of the canal. A potential advantage of cleaning and/or eroding the root canal using the flow of fluid includes the ability to reach locations such as curves, narrowings and/or branches of the root canal which otherwise would have been impossible or hard to reach, for example when using a file.

In some embodiments, root canal wall 303 is subjected to shear forces, which may be applied by flow 313. Optionally, due to the shear forces, a thin layer of tissue such as dentin tissue is removed by the flow. In some embodiments, the removal of tissue is homogenous. In some cases, for example in a narrowing and/or curvy portion of the root canal, the removal is non-homogenous. In some embodiments, homogenous removal depends on the diameter of root canal 305. For example, in a narrowing having a smaller diameter than 0.1 mm, removal may be non-homogenous. Optionally, in that case, a file may be used for widening the narrowing. In some embodiments, the thickness of the dentin layer removed by the flow of fluid ranges between 10-300 µm, for example 50 µm, 80 µm, 12 µm. Optionally, intermediate and/or lower thickness layers are removed. In some embodiments, the shear viscosity of the fluid affects the thickness of the removed layer.

In some embodiments, a rate of removal is controlled, for example, by applying shorter pulses, for example to prevent perforation. In some embodiments, imaging may be performed, for example during treatment, to decide if additional cleaning and/or abrading is needed.

In some embodiments, flow 313 reaches apex 319 of the root canal. In some embodiments, flow 313 may become turbulent along some portions of the root canal, for example in proximity to apex 319.

In some embodiments, flow 313 erodes apex 319, optionally resulting in a duller root canal. In some embodiments, the flow 313 is applied so that it does not widen a natural opening of the apex, for example ranging between 0.3-0.5 mm, 0.1-0.2 mm, 0.4-0.5 mm. Optionally, treatment duration is selected so that penetration of at least some of the flow through the apex is avoided.

In some embodiments, at least some portion of flow 313, optionally including the removed organic substance and/or debris, returns back up through the canal. Optionally, the flow passes along path 321, for example in a central lumen along vertical axis y. A potential advantage of the advancing and returning flow path may include the ability to use a large volume of fluid to clean the root canal. For example, a volumetric flow rate may range between 0.5-50 ml/sec, 10-30 ml/sec, 1-5 ml/sec.

In some embodiments, the velocity of flow 313 passing through root canal 305 may be affected by various parameters, such as the ratio between air and liquid of the fluid, the diameter of the root canal (which may vary along portions of the root canal), the viscosity of the fluid, the initial velocity of the fluid in the jet, and/or other parameters or combinations of them. Optionally, the velocity of flow 313 increases along some portions of the root canal, for example in a narrowing portion. In one example, the velocity of flow 313 advancing along the root canal wall is 0.5-50 m/sec. Optionally, the velocity of flow 313 changes according to a current location within the root canal. In some embodiments, the velocity of the flow enables a relatively high volumetric flow rate, for example 50 ml/sec.

Figure 4A:
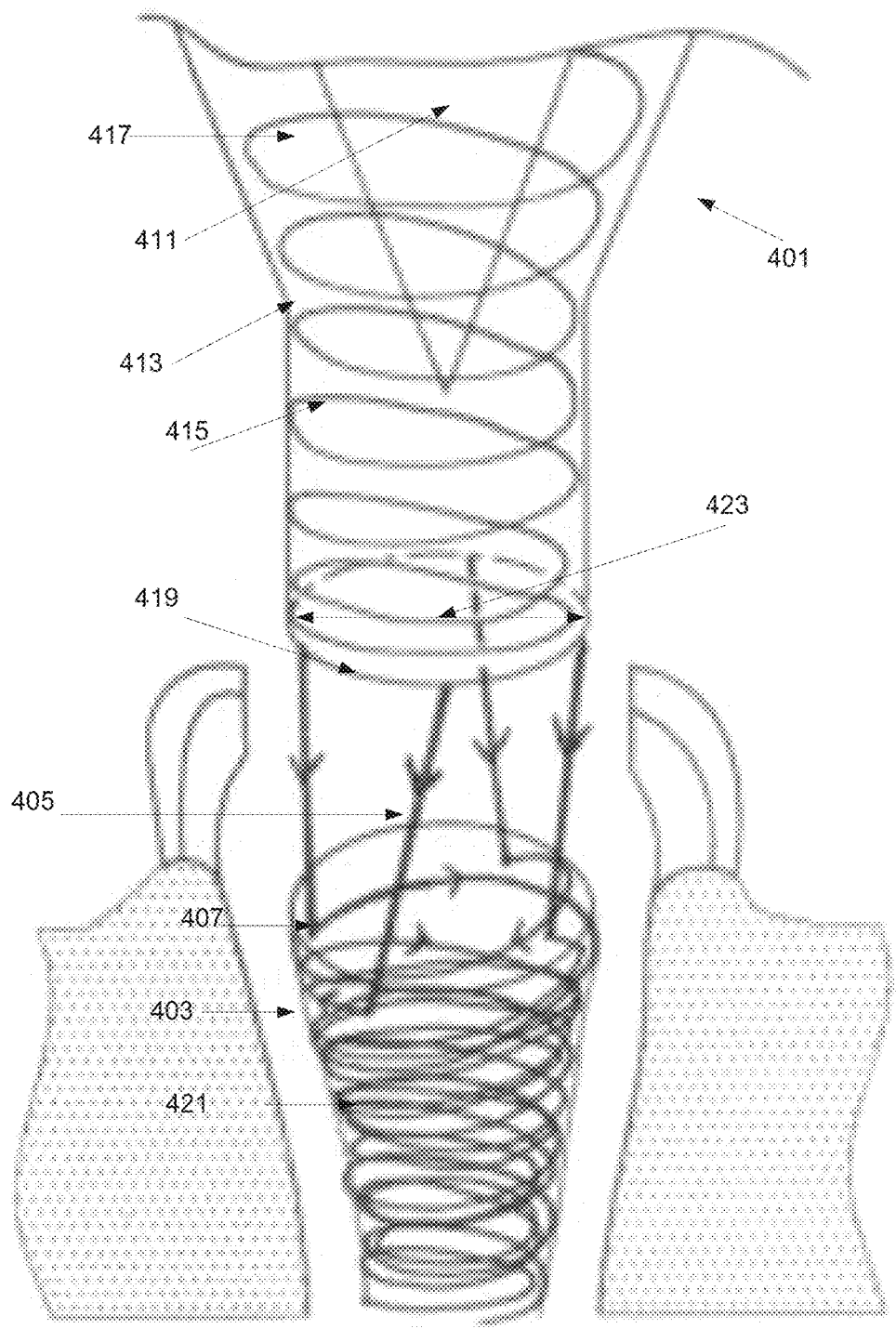
FIGS. 4A-4C are illustrations of a conical nozzle positioned at an entrance to a root canal, according to some embodiments of the invention.
Figure 4B:
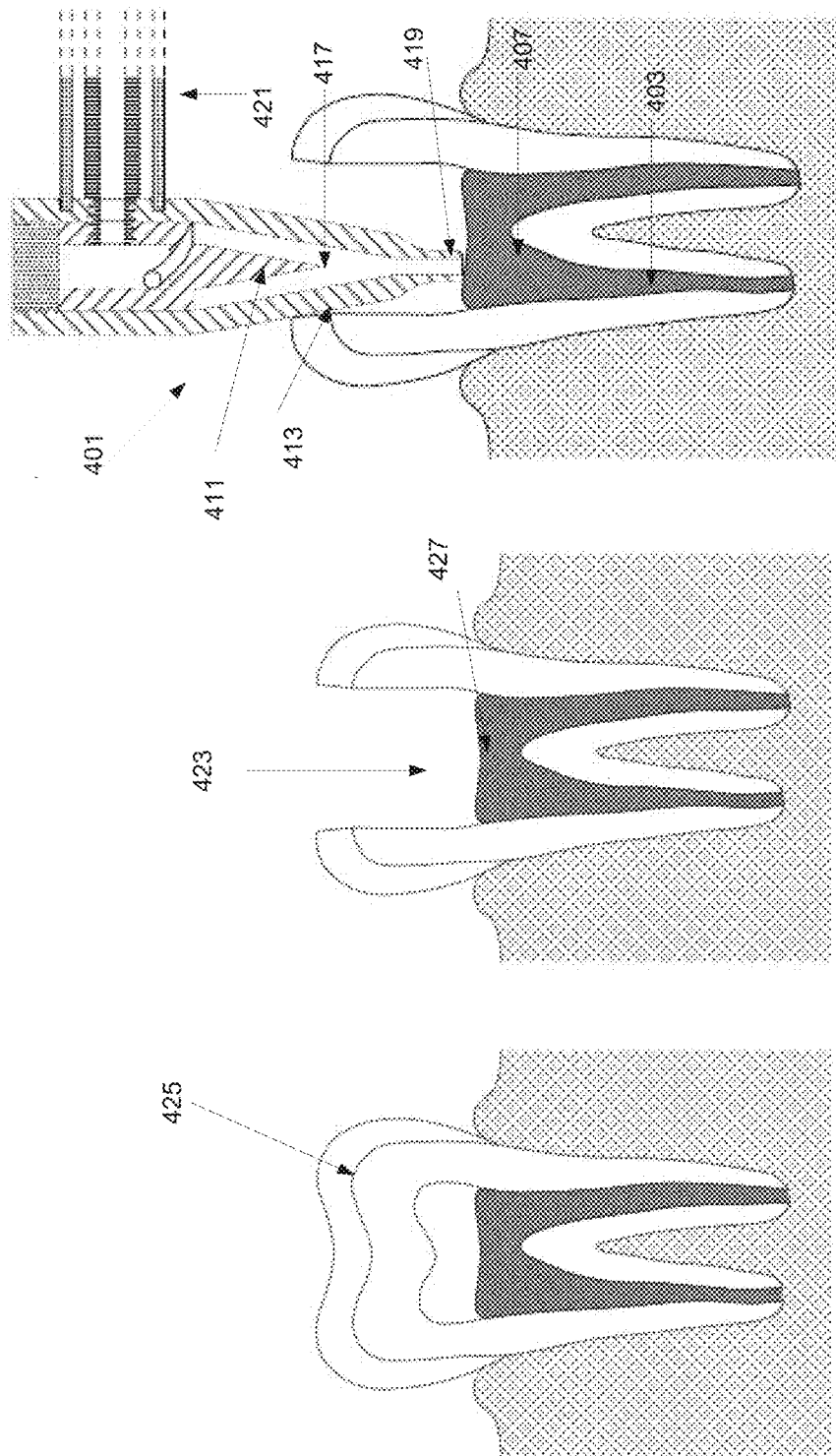
Figure 4C:
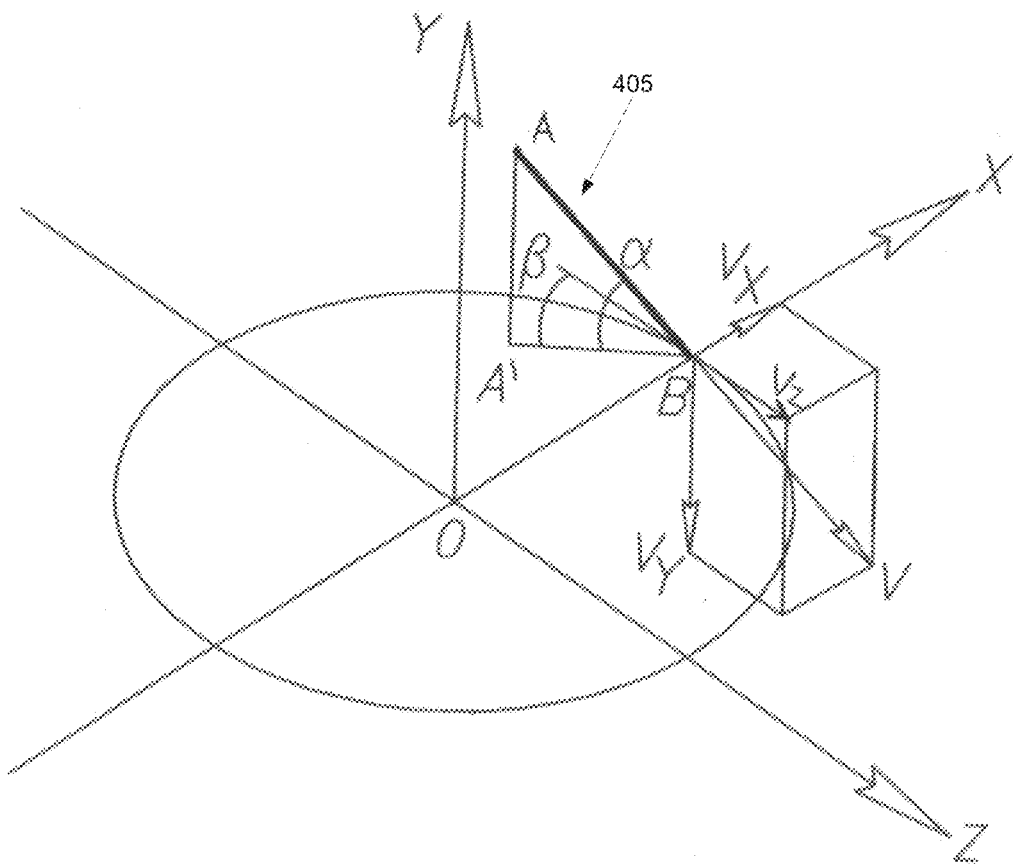

FIG. 4A illustrates a conical nozzle 401 positioned above the entrance to root canal 403, according to some embodiments of the invention. FIG. 4B illustrates an apparatus comprising conical nozzle 401 and a handle 421, positioned within access cavity 423 of a tooth above the entrance to root canal 403. FIG. 4C is a geometric representation of an angled fluid jet 405.

As seen in FIG. 4A, at least one angled fluid jet 405 is discharged from nozzle 401 and directed into entrance 407 of root canal 403.

In some embodiments, for example, as will be further described in FIG. 7, nozzle 401 includes one or more conical structures. Optionally, nozzle 401 includes an internal cone 411 positioned within an external cone 413. In some embodiments, circulating the fluid in a lumen between cones 411 and 413 creates the angled direction of fluid jet 405 or a plurality of fluid jets.

In some embodiments, the angled direction of fluid jet 405 or a plurality of fluid jets is obtained by the conical structure of nozzle 401. In an exemplary embodiment, fluid 415 flows into internal cone 411, passes (for example through a slanted tube as will be shown further on) into external cone 413, and circulates within a narrowing lumen 417 between external cone 413 and internal cone 411, until reaching exit aperture 419 of nozzle 401. In some embodiments, the velocity of the fluid is increased and/or decreased when circulating through the lumen, for example by changing the radius of the circulating path.

In some embodiments, nozzle 401 and/or exit aperture 419 of nozzle 401 are positioned above entrance 407 to root canal 403, for example 1 mm, 7 mm, 1 cm and/or intermediate or higher distances above. In some embodiments, exit aperture 419 is positioned vertically above entrance 407 such that a vertical axis y passes along a central longitudinal axis of nozzle 401 and of root canal 403. A potential advantage includes irrigating root canal 403 with one or more angled fluid jets 405 while nozzle 401 is positioned directly above entrance 407 of root canal 403. In some embodiments, nozzle 401 is positioned at an angle to vertical axis y.

In some embodiments, a diameter of angled jet 405 is smaller than a diameter 423 of exit aperture 419. For example, if a diameter of exit aperture 419 is 0.8 mm, a diameter of fluid jet 405 for example when passing through exit aperture 419 may be 10 µm, 90 µm 0.5 mm, 0.1 mm, 0.3 mm, and/or intermediate or lower diameters. In some embodiments, the diameter of angled jet 405 changes as it flows between exit aperture 419 and entrance 407 to the root canal.

In some embodiments, when a plurality of angled jets 405 are used, a distance between any pair of angled jets exiting through exit aperture 419 ranges between 0.01-3 mm, such as 0.05 mm, 0.8 mm, 2 mm. Optionally, this distance affects the formation of a coating-like layer of the flow of fluid advancing along root canal wall 421, for example, as described above.

In some embodiments, as fluid 415 circulates within lumen 417, a direction and/or magnitude of its momentum are determined by the structure of nozzle 401.

In some embodiments, one or more parameters are selected (by a dentist and/or manufacturer) to create the designated flow of fluid along the root canal wall for the removal of soft tissue. In some embodiments, these parameters include: the number of angled fluid jets, the pressure of the angled fluid jets, the velocity of the jets, the diameter of the jets, the viscosity of the fluid, the ratio between gas and liquid, the amount of abrasive powder added to the fluid, the duration of the treatment, the positioning of the nozzle, and/or any other parameters or combinations of them. In one example, the velocity and pressure of the fluid jet may be selected so that once the jet hits a wall at the root canal entrance, fluid does not spray beyond the entrance to the root canal, for example in the direction of the crown of the tooth. In some embodiments, parameters may depend on each other, for example the ratio between gas, liquid and/or may affect the viscosity of the fluid.

In some embodiments, as seen on FIG. 4B, an access cavity 423 is created, as previously mentioned, through crown 425 of the tooth. Optionally, access cavity 423 passes through layers of dentin and enamel tissue. In some embodiments, access cavity 423 exposes pulp chamber 427. In some embodiments, pulp chamber 427 is cleaned using the described system and/or method. Optionally, the pulp chamber is cleaned using other means. In some embodiments, the system and/or method as described are used for cleaning and/or abrading any other part of the tooth, but may have special advantages when used for treating a root canal.

In some embodiments, at least a portion of nozzle 401 passes through access cavity 423. In some embodiments, at least a portion of nozzle 401 is inserted through pulp chamber 427. In some embodiments, at least a portion of nozzle 401, for example the tip including exit aperture 419, is narrow enough to enter into at least a portion of the internal lumen of root canal 403.

In some embodiments, nozzle 401 is connected to a handle 421. In some embodiments, an input pipeline passes through handle 421 and connects to nozzle 401, as will be further explained. In some embodiments, handle 421 is used for maneuvering nozzle 401.

FIG. 4C is a geometrical representation of angled jet 405. In the described figure, angled jet 405 exits a nozzle at point A, and hits root canal wall at point B. In some embodiments, point B is located on a circumference of the root canal entrance. Alternatively, point B is located below the circumference of the root canal entrance, for example 0.1 mm, 1 mm, 3 mm and/or intermediate distances below.

As shown in this figure, axis x extends along a diameter of the root canal, perpendicular to the root canal wall. As mentioned herein, axis y is vertical axis running longitudinally, for example in parallel to the root canal wall. Axis z is perpendicular to both axis x and y. Line A'B is a projection of angled jet 405 on the xz plane. In some embodiments, an angle $\alpha$ between angled jet 405 (line AB) and the xz plane, is a sharp angle, for example an angle between 10-85°. In some embodiments, an angle $\theta$ between the projection A'B of angled jet AB and tangential axis z is a sharp angle, for example an angle smaller than 90°, such as 20°, 50°, 70°. In some embodiments, the size of angle $\beta$ affects the path of the flow. A potential advantage of a sharp angle $\beta$, for example ranging between 5-10°, 15-20°, includes creating a more effective flow path, in which the flow passes closely along the canal wall. Optionally, the size of angle β may affect the radii of the helical flow through the root canal. In some embodiments, angle β may be selected to encourage adhesion of flow to wall and/or reduce bouncing.

In some embodiments, a velocity vector V of angled jet 405 (line AB) can be described by its three velocity components along the axis, showed in this figure as Vx (along axis x), Vy (along axis y) and Vz (along axis z). In one example, velocity component Vy may be 2-50 m/sec, and the velocity component Vz may be 0.5-25 m/sec. In some embodiments, additionally and/or alternatively to the angled jets, an axial jet (for example extending in parallel to vertical axis y) may be used.

In some embodiments, any of the described above ideas and/or methods or combinations them may be implemented in the embodiments described below and/or any other embodiment of the invention.

Figure 5:
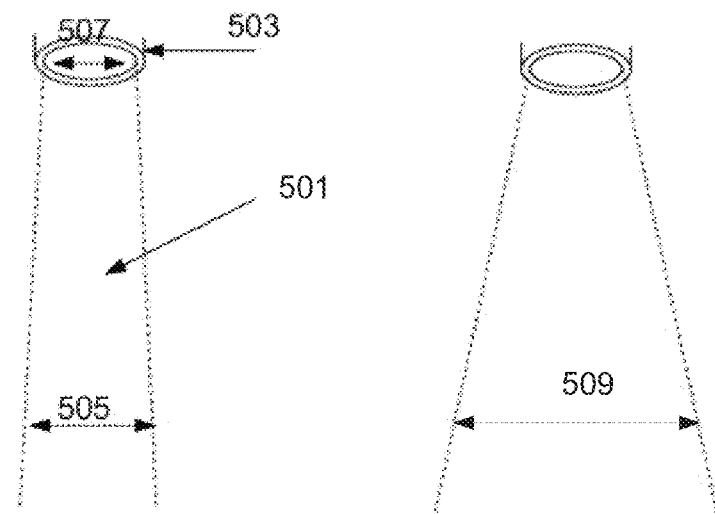
FIG. 5 is a side view of various outlines of a beam of angled fluid jets exiting a nozzle, according to some embodiments of the invention.

FIG. 5 shows a side view of various outlines of a beam 501 of angled fluid jets (not shown in this figure), according to some embodiments of the invention. The outlines of the beams shown in this figure describe beams that exit a nozzle 503, which have not yet entered a root canal.

In some embodiments, as previously described, a beam of a plurality of angled fluid jets is discharged from nozzle 503. In some embodiments, the structure of the nozzle affects the shape of the beam. In some embodiments, the size and/or shape of the tip of the nozzle affects the shape of beam. For example, an elongated tip, as will be further shown, may be used to create a narrower, focused beam of angled jets. Alternatively, a shorter tip may be used to create a more scattered beam of angled jets.

In some embodiments, a diameter 505 of a beam extends beyond a diameter 507 of the exit aperture of the nozzle. In some embodiments, as shown in this figure, a diameter of the beam changes, for example increases as the flow advances towards the root canal entrance. Optionally, this outline is created due to opposite angled jets (for example jets exiting from opposite ends of a diameter of the nozzle). In some embodiments, for example as shown in this figure, various beams may have different diameters at a certain axial distance from the exit aperture of the nozzle. For example, diameter 505 is shorter than diameter 509.

In some embodiments, for example when an exit aperture of the nozzle is positioned within a lumen of the root canal, the jets of the beam may immediately hit the root canal wall, which may channel the fluid to a helical flow along the wall.

In some embodiments, the designated flow along the root canal wall is a result of the original direction in which the angled jets exit the nozzle, and/or a result of the angle created when the jets hit the root canal.

In some embodiments, at least some of the angled jets flow in the same direction.

In some embodiments, a ratio between air and liquid affects the shape of the beam. Optionally, the fluid density affects the shape of the beam.

In some embodiments, the outline of the beam may have other shapes such as, for example, a bottle-neck shape, a cylindrical shape, a bell shape, and/or any other shapes.

Figure 6A:
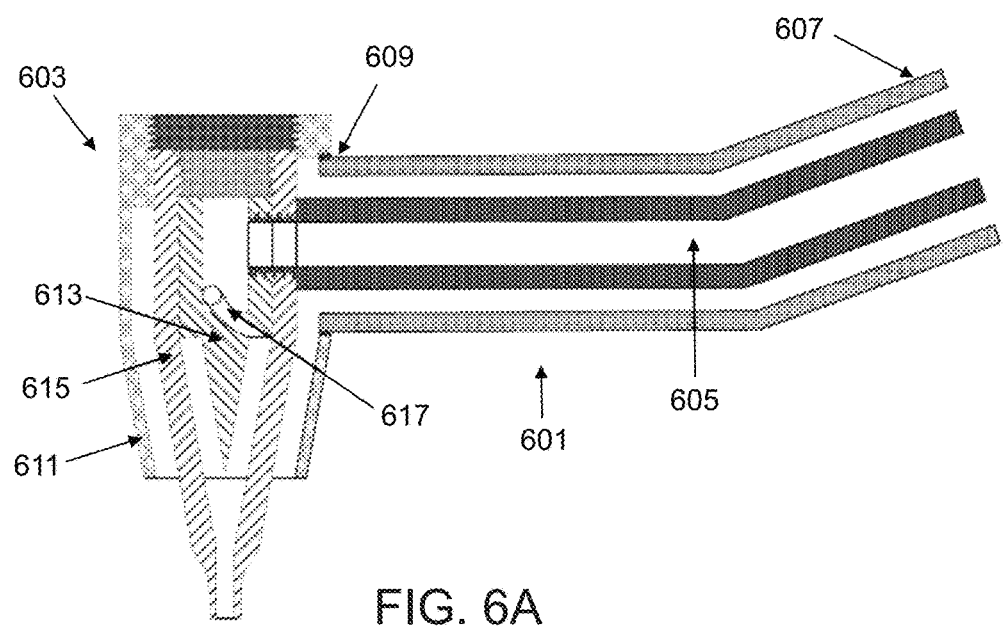
FIGS. 6A-B are a cross section and an outline view of an apparatus comprising a handle and a conical nozzle, according to some embodiments of the invention.
Figure 6B:
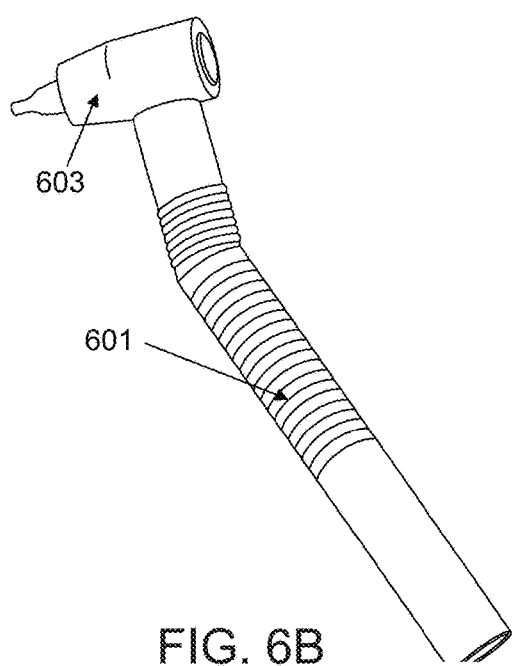

FIG. 6A is a cross section view of an embodiment of an apparatus comprising a handle 601 and a nozzle 603, for cleaning and/or abrading a root canal with one or more angled fluid jets. FIG. 6B is an outline of the apparatus comprising the handle and nozzle.

In some embodiments, handle 601 comprises one or more pipes 605, optionally passing longitudinally along an internal lumen of the handle.

In some embodiments, pipe 605 ends at its distal end in an entrance aperture to nozzle 603, for example an entrance aperture leading to an internal cone of the nozzle, as will be further described.

In some embodiments, a proximal end 607 of handle 601 is configured for manual gripping by a user.

In some embodiments, a distal end 609 of handle 601 connected to nozzle 603 is configured for insertion into a tooth, for example through a pulp chamber, to allow the positioning of an exit aperture of nozzle 603 above a root canal entrance as previously described. Optionally, handle 601 comprises a narrowing portion in proximity to nozzle 603 (not shown in this figure), which may facilitate inserting distal end 609 through, for example, an access cavity created in a tooth. In some embodiments, a height of the nozzle is small enough to enable its insertion into the mouth, for example ranging between 5-15 mm.

In some embodiments, inner pipe 605 extends beyond the proximal end 607 of handle 601. Optionally, liquid passes through inner pipe 605, for example by being connected at the proximal end to a liquid tank. Optionally, air passes through inner pipe 605, for example by being connected at the proximal end to an air compressor. In some embodiments, the fluid comprising both air and liquid passes through pipe 605. In some embodiments, two pipes are used, one for passing liquid and the other for passing air. In some embodiments, air and abrasive powder (for example transferred from an abrasive powder tank) pass together through at least one of the pipes. In some embodiments, a pipe may be surrounded by another pipe (co-centered pipes), such that the inner pipe is used, for example, for transferring liquid, and the outer pipe is used, for example, for transferring air. In some embodiments, air, liquid, abrasive powder and/or combinations of them pass through at least one of the pipes through the handle.

In some embodiments, the pipes may connect, for example at the proximal end 607 of handle 601, to create the fluid of air and liquid which then circulates within nozzle 603 until discharged in the form of angled jets.

In some embodiments, nozzle 603 has conical structure, for example, as will be explained in the following figure. In some embodiments, nozzle 603 comprises an internal cone 613 positioned within an external cone 615. In some embodiments, a slanted tube 617 is used for passing fluid from internal cone 613 to a lumen between the two cones, for example, as will be explained by the next figure.

In some embodiments, nozzle 603 comprises an additional cone 611, for example used for suctioning the fluid returning upwards through the root canal, for example, as will be further explained in FIG. 10. In some embodiments, the sucked fluid may pass through the handle, for example passing in an opposite direction to the air and/or liquid passed into nozzle 603. Optionally, the sucked fluid passes through one or more pipes in the handle. Optionally, proximal end 607 of handle 601 is connected to a pipe and/or tank and/or any other element used for disposing the sucked fluid.

In some embodiments, the nozzle and/or any components of it and/or the handle may be made of various materials, such as, for example, one or more of stainless steel, titanium, aluminum, anodized coated aluminum, PPM, plastic, or other biocompatible and/or sterilizable materials and/or combination of materials. In some embodiments, at least a part of the nozzle and/or handle is disposable. In an exemplary embodiment of the invention, the nozzle is formed of rigid materials and/or geometries, however, a tip thereof may be made flexible.

In some embodiments, the nozzle may be manufactured and/or used separately from the handle and/or the rest of the system, described below.

In some embodiments, the handle may comprise controls such as on/off button to control the duration of the treatment, a dial to control the ration between air and liquid, etc.

Figures 7A, 7B:
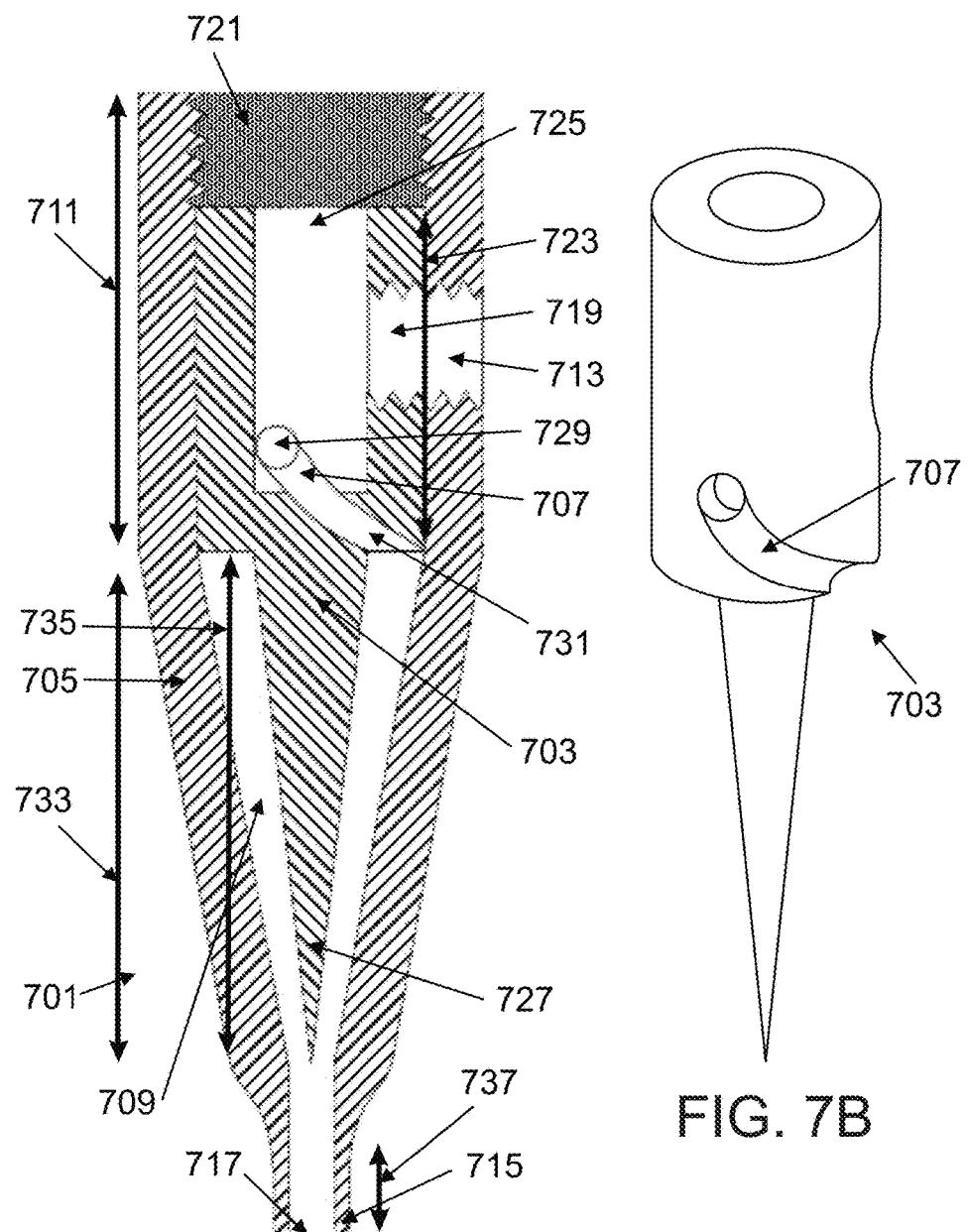
FIGS. 7A-7B are a cross section of a conical nozzle and a side view of an internal cone configured within the conical nozzle, according to some embodiments of the invention.

FIG. 7A is cross section view of a conical nozzle 701, and FIG. 7B a side view of an internal cone 703 configured within conical nozzle 701, according to some embodiments of the invention.

In some embodiments, nozzle 701 comprises an internal cone 703 positioned within an external cone 705. In some embodiments, internal cone 703 and external cone 705 are connected by a tube, for example a slanted tube or channel 707 extending between an inner lumen of internal cone 703 and a lumen 709 between an external face of internal cone 703 and an internal face of external cone 705.

In some embodiments, external cone 705 has a cylindrical upper portion 711. In some embodiments, external cone 705 has a recess 713 for example configured along a face the cylindrical upper portion 711, optionally in continuance to a pipe of a handle as described above, for allowing fluid to enter into internal cone 703. In some embodiments, the recess may be circular, triangular, rectangular or any shape allowing the flow of fluid through into internal cone 703. Optionally, the size and/or shape of the recess is determined according to the size and/or shape of an entrance aperture 719 to internal cone 703.

In some embodiments, external cone 705 has an exit aperture 715, which may be positioned above the entrance to a root canal. In some embodiments, the exit aperture may is circular, for example having a diameter 717 ranging between 0.3-2 mm. Optionally, the diameter of the exit aperture is determined according to a need, for example according to a diameter of the root canal entrance.

In some embodiments, external cone 705 comprises a narrow needle-like tip portion 737. In some embodiments, the length of narrow needle-like tip portion 737 ranges between 0.2-7 mm. In some embodiments, narrow tip 737 (comprising exit aperture 715) is inserted into a lumen of the root canal. Optionally, narrow tip portion is inserted to a distance of 0.2 mm, 0.5 mm, 1 mm, 2.5 mm and/or any intermediate or higher distances measured longitudinally from the root canal entrance. In some embodiments, an external diameter of tip portion 737 ranges between 0.5-2.5 mm, and an internal diameter (optionally being the diameter of the exit aperture, as previously mentioned) ranges between 0.3-2 mm. in some embodiments, the diameter of tip portion 737 is small enough to allow insertion of tip portion 737 into at least a portion of the root canal. Optionally, tip portion 737 is flexible, for example made of flexible material.

In some embodiments, cylindrical upper portion 711 is covered by a covering lid 721, for example for preventing fluid from exiting through the top of nozzle 701.

In some embodiments, covering lid 721 may be screwed on top of the cylindrical upper portion 711.

In some embodiments, internal cone 703 comprises a cylindrical upper portion 723, which may be sized and/or shaped according to cylindrical upper portion 711 of external cone 705.

In some embodiments, internal cone 703 comprises an entrance aperture 719, for example configured along a face of the cylindrical upper portion 723. In some embodiments, entrance aperture 719 is configured in continuance to recess 713 of external cone 705. In some embodiments, the entrance aperture may be circular, triangular, rectangular or any shape allowing the flow of fluid through.

In some embodiments, cylindrical upper portion 723 fits within cylindrical upper portion 711 such that no space is formed between them, for example preventing fluid from flowing between the two upper portions of the cones. In some embodiments, a diameter of cylindrical upper portion 723 is only slightly smaller than a diameter of cylindrical upper portion 711. For example, a diameter of cylindrical upper portion 723 ranges between 2-18 mm and a diameter of cylindrical upper portion 711 ranges between 3-20 mm.

In some embodiments, a top 725 of cylindrical upper portion 723 is open. In some embodiments, if cylindrical portion 723 of internal cone 703 extends to the same height as cylindrical portion 711, covering lid 721 may cover both internal and external cones.

In some embodiments, a tip 727 of internal cone 703 is closed, to avoid fluid from passing through. In some embodiments, tip 727 extends to exit aperture 715, and/or extends beyond exit aperture 715, for example 1 mm beyond.

In some embodiments, a slanted tube 707 extends between an inner lumen of internal cone 703 and a lumen 709 between an external face of internal cone 703 and an internal face of external cone 705. Optionally, the entrance 729 to slanted tube 707 serves as the exit aperture for the fluid exiting internal cone 703. Optionally, exit 731 of slanted tube 707 is configured at the lowest point along a face of the cylindrical upper portion 723, such that it leads to lumen 709.

In some embodiments, the size of lumen 709 is determined according to a difference in diameters of narrowing portions 733 and 735 of external cone 705 and internal cone 703 respectively. For example, an initial diameter of narrowing portion 733 is 3 mm and an initial diameter of narrowing portion 735 is 0.3 mm. In some embodiments, a distance between the internal and external cones forming lumen 709 is constant, for example a distance of 1 mm. In some embodiments, a distance between the internal and external cone changes, for example increases along a vertical axis.

In some embodiments, fluid, optionally including liquid, air, and/or abrasive powder or combinations of the above, flows through recess 713 of external cone 705, into entrance aperture 719 of internal cone 703, and into a lumen of internal cone 703. In some embodiments, as the fluid accumulates within internal cone 703, pressure may rise and the fluid may be forced through entrance 729 into slanted tube 707. Once the fluid exits slanted tube 707 through exit 731, the fluid circulates within lumen 709 between the internal and external cones. Optionally, the circulation is helical. Optionally, as the lumen narrows, the velocity of the flow of fluid increases. In some embodiments, the helical circulation causes the fluid to exit nozzle 701 through exit aperture 715 of external cone 705 in the form of one or more angled fluid jets as describe above.

In some embodiments, due to the ratio between air and liquid, for example 90% air and 10% liquid, the fluid entering lumen 709 is an aerosol. A potential advantage of the aerosol includes reducing the friction created between the surface of the cones and the fluid, which may optionally allow for a higher velocity of the fluid (aerosol).

In some embodiments, any of the cones may be nonsymmetrical and/or otherwise distorted.

Figure 8A:
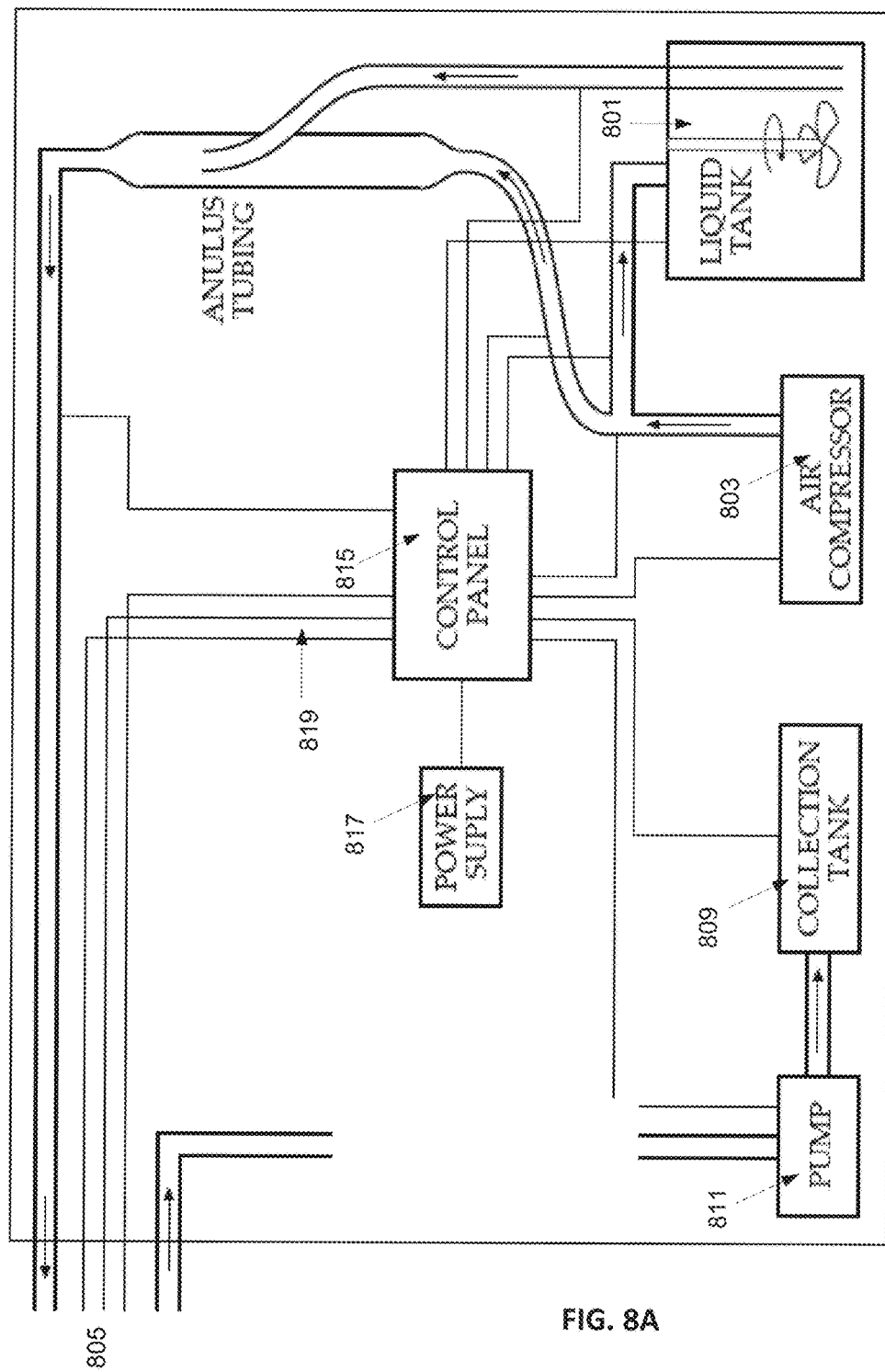
FIGS. 8A-8B are schematic diagrams of exemplary systems for treating a root canal, according to some embodiments of the invention.
Figure 8B:
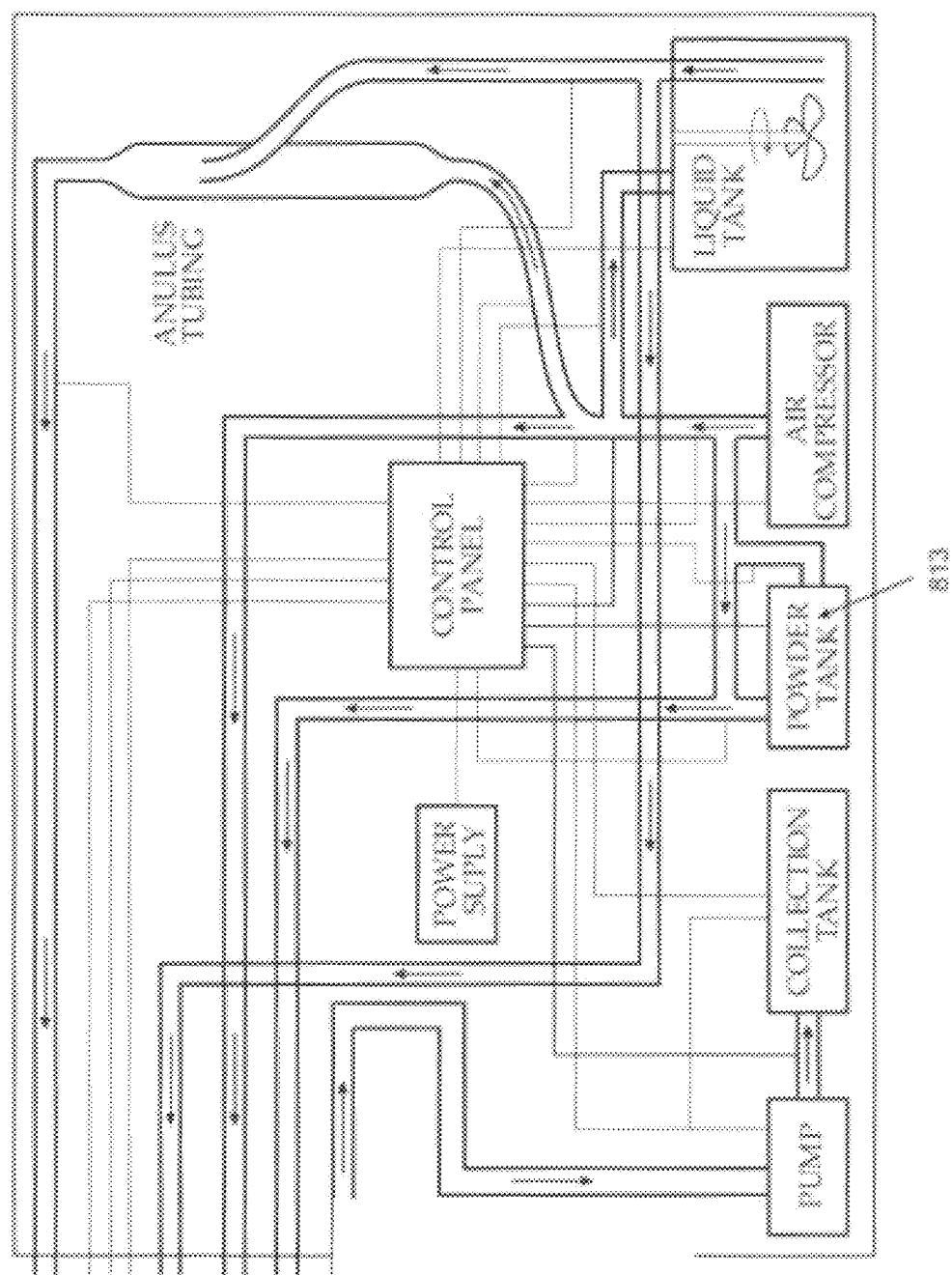

FIGS. 8A and 8B are schematic diagrams of exemplary systems for treating a root canal, according to some embodiments of the invention.

In some embodiments, the system comprises a liquid tank 801, for example for storing liquid such as water, disinfectant, and/or medicine. Optionally, more than one liquid tank is used, for example for storing medicine separated from water, or disinfectant separated from medicine. In some embodiments, the capacity of the liquid tank ranges between 0.2-50 L. In some embodiments, the liquid tank may be made of aluminum, steel, plastic, or any material capable of containing the liquid and withstanding air pressure. In some embodiments, liquid tank 801 may comprise a mixing element, such as a mechanical, hydraulically, or electrical whirling element for continuous mixing of the liquid.

In some embodiments, liquid tank 801 is connected to an air compressor 803. In some embodiments, the air compressor pushes air into liquid tank 801. In some embodiments, the pressure created by the air compressor ranges between 5-500 PSI, 1-100 PSI, 100-200 PSI. Optionally, as the air compressor pushes air into the liquid tank, the pressure rises within the tank and liquid is forced through an exit aperture of the tank. In some embodiments, the exit aperture of the tank is connected a handle 805 of an apparatus as described above, for example connected by a pipe.

In some embodiments, the system comprises a collection tank 809. Optionally, collection tank 809 is used for the returning fluid exiting the root canal, which may comprise organic substance, nonorganic substance, and/or debris. In some embodiments, collection tank 809 is connected to a pump 811 and/or to a venturic connector. In some embodiments, the pump is used for suctioning the returning fluid, for example through a suctioning cone of a nozzle (not shown in this figure), through handle 805, and through one or more pipes leading to collection tank 809. Optionally, a suction cap may be placed on the tooth and/or inside the mouth for collecting returning fluid, saliva, and/or debris.

In some embodiments, as shown in FIG. 8B, a powder tank 813 is used for storing the abrasive powder. In some embodiments, powder tank 813 is connected to air compressor 803.

Air, liquid, abrasive powder and/or any combinations of them may pass through one or more pipes of the system.

In some embodiments, as shown in FIG. 8A, a pipe connected to air compressor 803 and a pipe connected to liquid tank 801 are joined at any point along a path leading to handle 805, so that the air and liquid are mixed together before entering handle 805. In some embodiments, as shown in FIG. 8B, a plurality of pipes may lead air, liquid, abrasive powder and air, liquid and air and/or any combination of them into handle 805.

In some embodiments, liquid and air or any other combination may flow through co-centered pipes.

In some embodiments, a pipe includes micro pores, for example allowing air to flow inside but preventing liquid from exiting the pipe.

In some embodiments, any of the above described components and/or combinations of them are passed separately, and mixed together only at a lumen of the nozzle (not shown in this figure).

In some embodiments, a control panel 815 is used for example for controlling the passing of air, liquid, and/or abrasive powder. In some embodiments, pressure, velocity, volume, flow rate and/or any other parameters may be controlled. In some embodiments, the duration of treatment is controlled using control panel 815. In some embodiment, control panel 815 may be connected to a power supply 817.

In some embodiments, two or more components of the system such as the liquid tank, air compressor, pump, and/or any other components are connected by an electrical circuit 819. In some embodiments, control panel 815 is used for activating electrical circuit 819 to control the functioning of one or more components of the system. For example, an electrical signal may be sent using control panel 815 to activate air compressor 803, to release liquid from liquid tank 801, to pass fluid into the handle, open a valve along a pipe or junction, and/or any other functions of the system.

FIGS. 9A-9D illustrate an embodiment of a conical nozzle 901 comprising a pipe 903, extending between handle 905 and exit aperture 907 of nozzle 901.

Figure 9C:
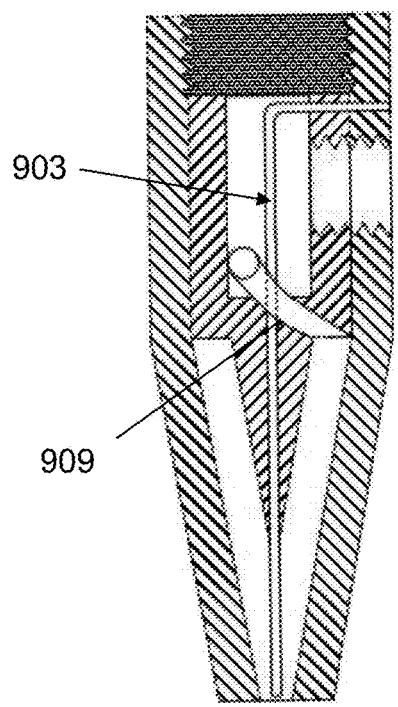
Figure 9D:
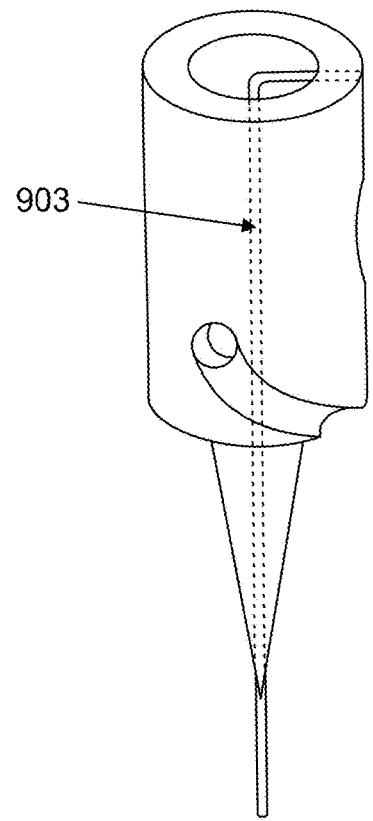

FIGS. 9A and 9B illustrate two embodiments including pipe 903. FIG. 9B shows conical nozzle 901 having a narrow tip portion 911 as previously described. FIG. 9A conical nozzle 901 having flat tip portion 913. FIG. 9C is a cross section of a nozzle similar to the one described in the above figures that further includes pipe 903. FIG. 9D is a side view of an internal cone of that nozzle.

In some embodiments, longitudinal pipe 903 is used for passing air, abrasive powder, liquid and/or combination of them flow through nozzle 901. In some embodiments, flowing is performed through pipe 903 in parallel to a fluid flowing through a main path of nozzle 901, as described above.

In some embodiments, a distal portion of pipe 903 protrudes from exit aperture 907. In some embodiments, for example as shown in FIG. 9B, if narrow tip portion 911 is inserted into at least a portion of the root canal, pipe 903 may be used for delivering any of the above materials into a location within the root canal.

In some embodiments, pipe 903 affects the direction of the discharged angled fluid jets by diverting them.

In some embodiments, a proximal end of pipe 903 is connected to any of the above described components of the system, such the fluid tank, the air compressor, the powder tank and/or any of the pipes.

In some embodiments, the internal and external cones comprising nozzle 901 include an aperture 915 for the passing of pipe 903, for example configured along a face of the upper cylindrical potion of both cones, such as above or below a recess 917 and entrance aperture 919 of the external and internal cones respectively.

In some embodiments, as shown on FIGS. 9C and 9D, pipe 903 passes on a parallel plain to slanted tube 909. In some embodiments, pipe 903 intersects tube 909, for example to enable mixing of the fluid with the substance passing through pipe 903.

Figure 10A:
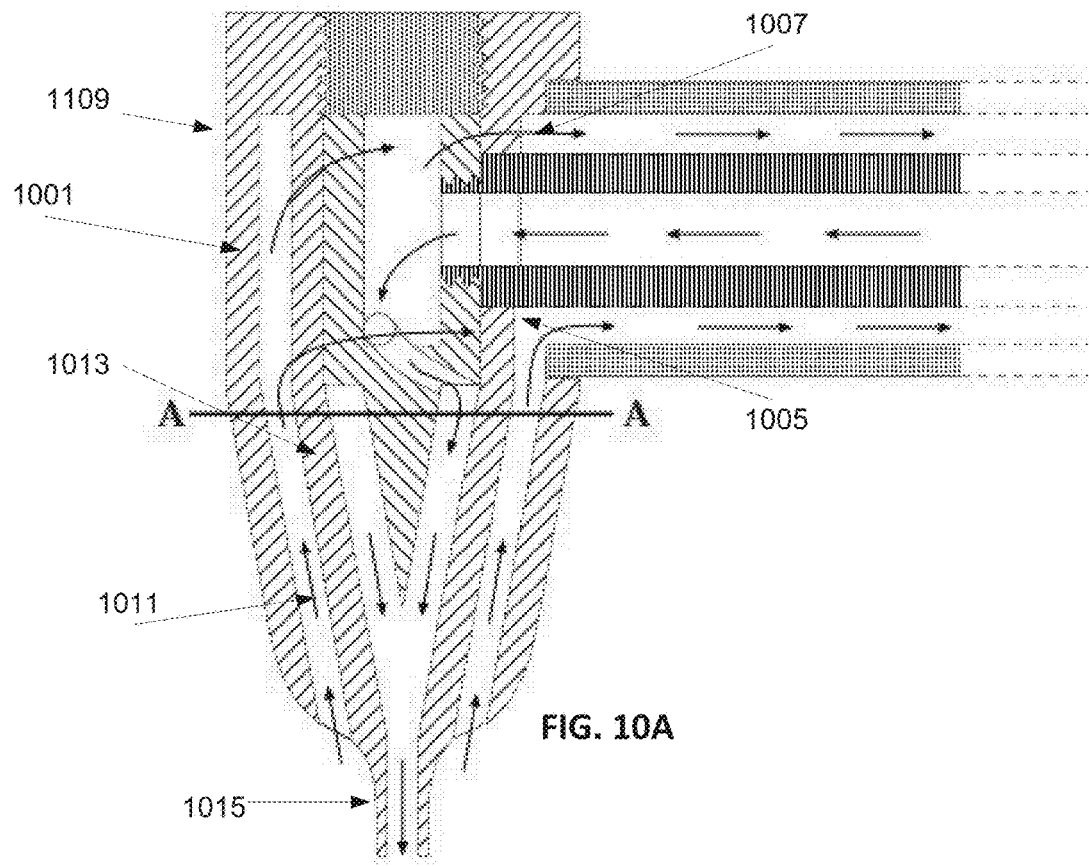
FIGS. 10A-10B are illustrations of a nozzle comprising a suction cone, and a horizontal cross section of the nozzle respectively.
Figure 10B:
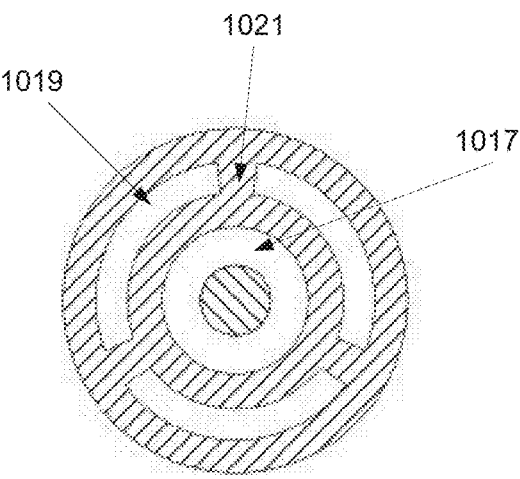

FIG. 10A illustrates a nozzle comprising a suction cone 1001, as previously mentioned, and FIG. 10B illustrates a horizontal cross section of the nozzle.

In some embodiments, suction cone 1001 is shaped and/or sized according to an external cone and/or an internal cone of the nozzle.

In some embodiments, suction cone 1001 is assembled externally to the nozzle. In some embodiments, suction cone is attached to the nozzle during a molding process. In some embodiments, other mechanical means such as pins or screws are used for attaching the suction cone.

Optionally, a lumen 1011 is formed between the narrowing portions of suction cone 1001 and an external cone 1013 of the nozzle. In some embodiments, this lumen comprises channels or tubes.

In some embodiments, the distal tip of the nozzle 1015 protrudes from suction cone 1001.

In some embodiments, suction cone 1001 has one or more exit apertures 1005 and/or 1007. Optionally, exit apertures 1005 and/or 1007 are configured along a cylindrical upper portion 1009 of suction cone 1001. In some embodiments, exit apertures 1005 and/or 1007 are connected to handle, optionally through pipes. In some embodiments, the pipes are connected to a pump such as a vacuum pump for sucking the returning fluid upwards through the nozzle and through the handle to dispose it, as previously described in FIG. 8.

In some embodiments, the sucked fluid may pass through suction cone 1001 in a lumen between an internal face of the suction cone and an external face of the external cone of the nozzle. In some embodiments, if the lumen comprises channels or tubes, the fluid may be sucked directly through the tubes.

In some embodiments, the fluid returning upwards through the root canal may contain the removed organic and/or inorganic substances such as pulp tissue, nerve tissue, blood vessels, abrasive powder, and/or other debris removed by the flow.

In some embodiments, suction cone 1001 is covered by a lid, which is optionally screwed on top of a lid of the external cone of the nozzle to prevent fluid from exiting through the top of suction cone 1001.

FIG. 10B shows a horizontal cross section of the nozzle along line AA. A central circular lumen 1017 is the lumen formed between the internal and external cones. The three arched lumens 1019 are the lumens formed between the external cone and suction cone 1001. In some embodiments, a space 1021 between arched lumens includes anchors for attaching suction cone 1001 to the narrowing portion of the nozzle.

Figure 11A:
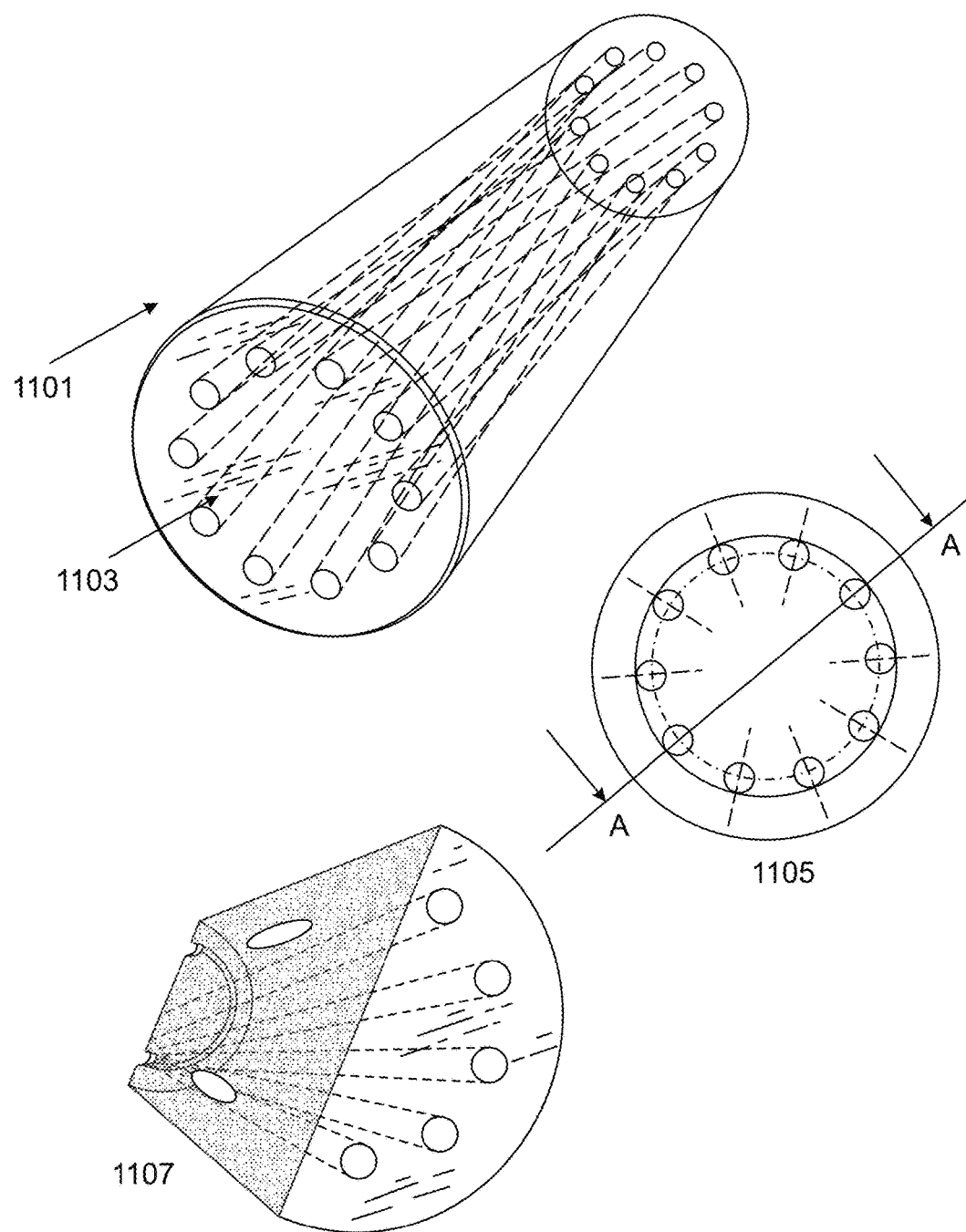
FIGS. 11A-11B are illustrations of a nozzle including one or more directing channels for creating the one or more angled fluid jets, according to some embodiments of the invention.
Figure 11B:
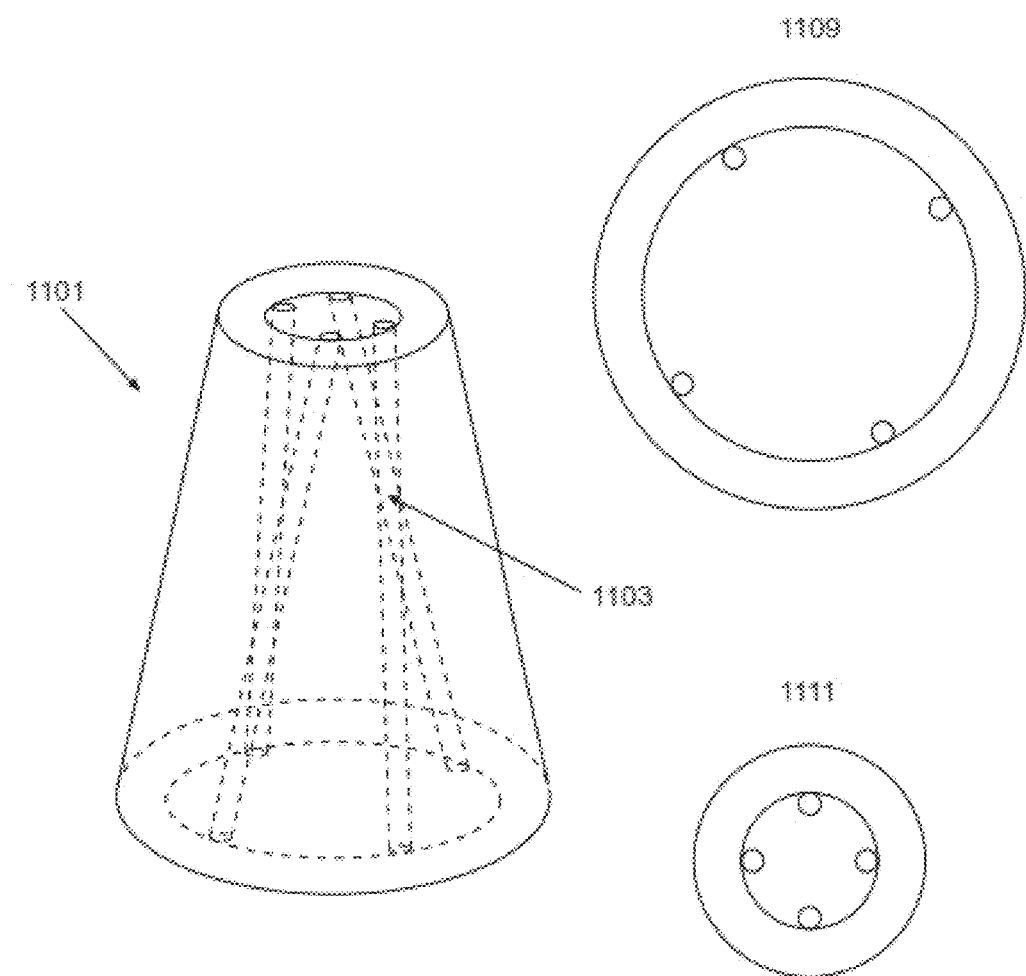

FIG. 11A-B show two embodiments of a nozzle including one or more directing channels for creating the one or more angled fluid jets, according to some embodiments of the invention. FIG. 11A includes a nozzle 1101, a horizontal cross section of the distal end of the nozzle 1105, and a longitudinal cross section of the nozzle 1107. FIG. 11B includes a conical nozzle 1101, a horizontal cross section 1109 of the distal tip of the nozzle (exit aperture), and a horizontal cross section 1111 of the proximal tip of the nozzle.

In some embodiments, a nozzle 1101 of an apparatus may comprise one or more channels for directing the angled fluid jets. In some embodiments, the channels are formed as tubes 1103. In some embodiments, nozzle 1101 is a cylinder. In some embodiments, tubes 1103 are configured along the internal wall of nozzle 1101.

In some embodiments, an angle of the tube is determined according to a resulting angle of the fluid jet formed by the tube. In some embodiments, the configuration (such as angle) of the tube is adjustable, for example by connecting a back plate of a tube using a screw to the wall of nozzle 1101.

In some embodiments, tubes 1103 have a similar diameter. In some embodiments, tubes 1103 have various diameters. In some embodiments, a single tube may change in diameter.

Figure 12A:
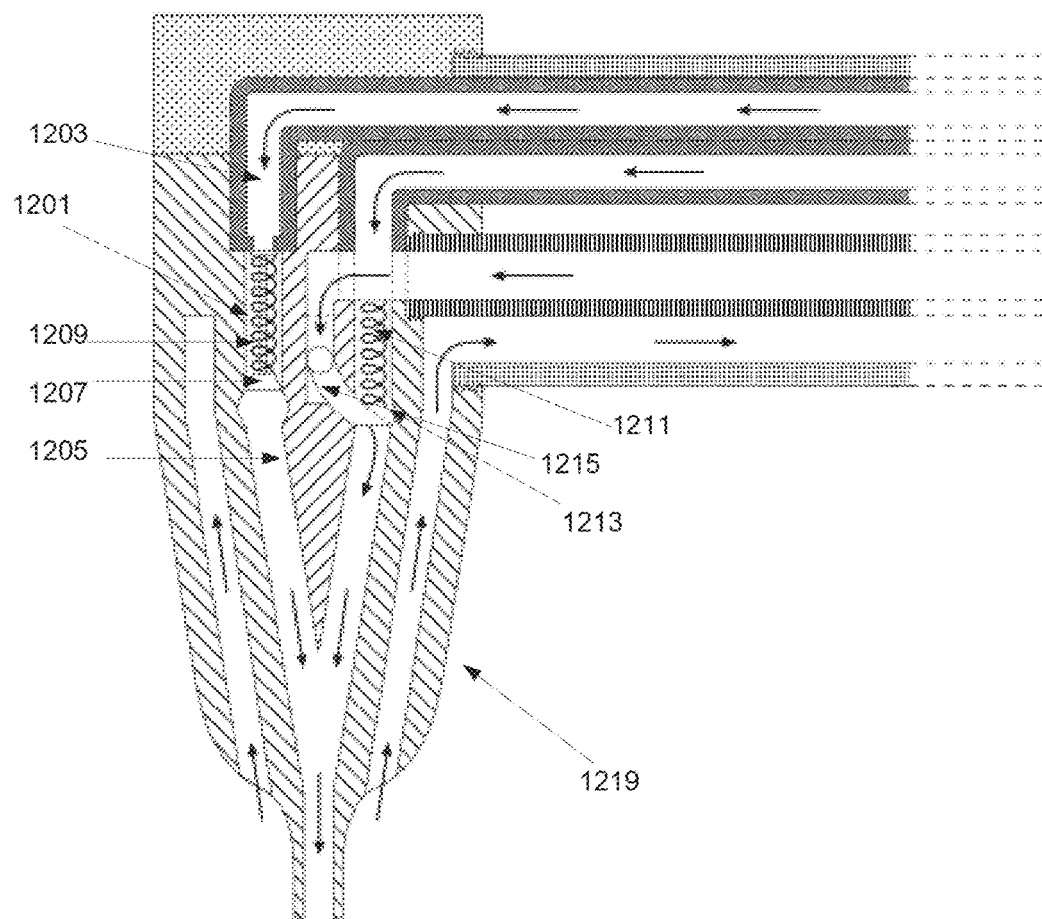
FIGS. 12A-12C are illustrations of a nozzle comprising a valve for controlling the flow through the nozzle, according to some embodiments of the invention.
Figure 12B:
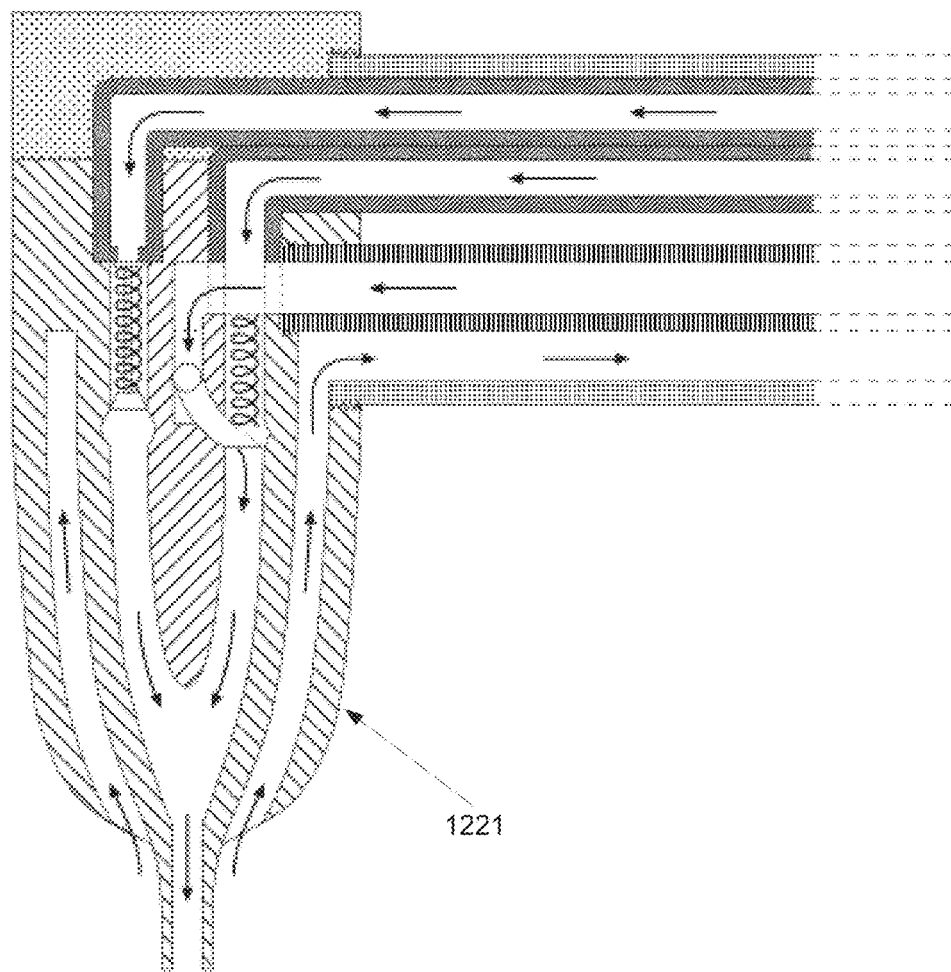
Figure 12C:
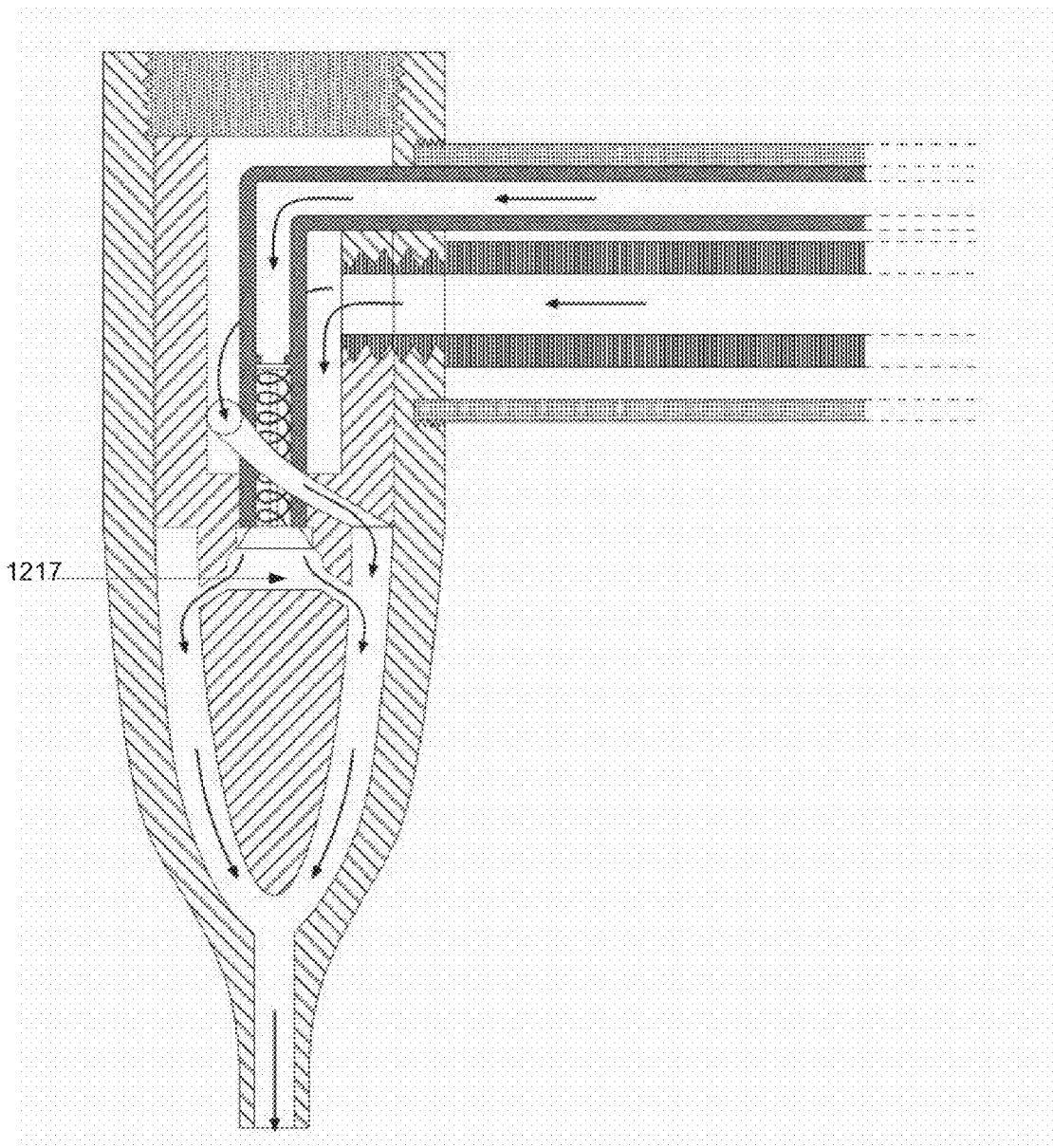

FIGS. 12A-12C are drawings of a nozzle comprising at least one valve for controlling the flow through the nozzle, according to some embodiments of the invention. In FIG. 12A, the nozzle has conically shaped outline 1219, and in FIG. 12B, the nozzle has an elliptically shaped outline 1221. In both FIGS. 12A and 12B, the nozzle is formed as one piece, for example formed using molding methods. In FIG. 12C, the nozzle may be formed of separate components, for example cones connected together, as will be further explained.

In some embodiments, a valve 1201 is used for controlling flow, for example the flow of air (or any other gas), liquid, abrasive powder and/or combinations of those into the nozzle. In some embodiments, as shown in FIGS. 12A and 12B, valve 1201 is positioned between the end of a pipe 1203 passing through the handle, and the lumen 1205 formed between an external and internal cones of the apparatus. In some embodiments, as shown in FIG. 12C, valve 1201 is positioned between the end of pipe 1203 and a connecting lumen 1217. Optionally, when the valve is in open position, a flow of any of the above substances and/or combinations of them enters connecting lumen 1217, from which it then passes to lumen 1205. Additionally and/or alternatively, at least one valve may be positioned between connecting lumen 1217 and lumen 1205. Additionally and/or alternatively, a valve is positioned at any junction, entrance aperture, exit aperture, along a pipe, a lumen of the nozzle, or any other portion of the nozzle.

In some embodiments, valve 1201 comprises a sealing element 1207. In some embodiments, the sealing element prevents fluid and/or any other substance from flowing upwards into pipe 1203.

In some embodiments, valve 1201 comprises a spring 1209. In some embodiments, the spring extends or compresses due to air and/or liquid pressure. In some embodiments, spring 1209 and/or sealing element 1207 is controlled using other means, such as mechanical means (for example by connecting valve 1201 to a lever controlled from the handle), hydraulic means (operated for example by the pressure of fluid passing through) and/or electrical means.

In some embodiments, when spring 1209 extends, it pulls sealing element 1207 into an open position. Optionally, in the open position, a material such as air, liquid, abrasive powder and/or combinations of them may flow into lumen 1205.

Additionally and/or alternatively, a valve 1211 is used for controlling the flow of fluid from a lumen of the internal cone into lumen 1205 between the external and internal cones. Optionally, sealing element 1213 of the valve is positioned at the end of slanted tube 1215. In some embodiments, this valve is used for controlling the treatment duration, for example by periodically pushing the valve to a closed position.

In some embodiments, other elements such as a cord may be used instead of a spring. In some embodiments, only sealing element 1207 may be used, for example formed as a flap which opens due to air pressure.

A potential advantage of using valve 1201 or similar includes the ability to add any substance to the fluid immediately before the fluid enters the root canal. In one example, abrasive powder that may dissolve in fluid, such as salt, may be passed (with or without air) through pipe 1203, and enter lumen 1205. Optionally, since the addition of salt to the fluid is performed at a relatively short time before entering the root canal, a portion of the salt does not dissolve and can be used as abrasive powder for the removal of soft tissue from the root canal.

Figure 13D:
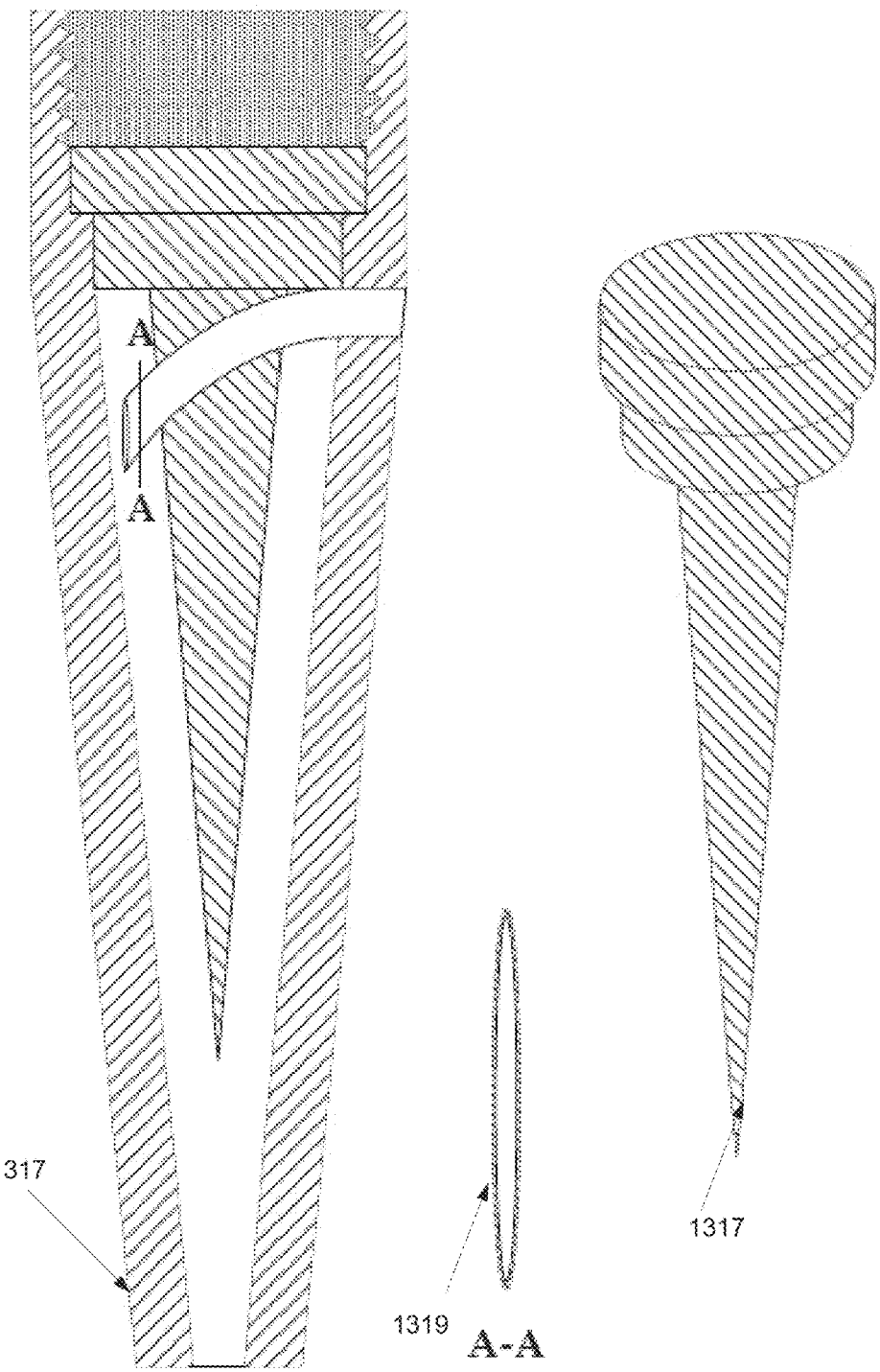

FIG. 13A-13D illustrate a nozzle comprising a cone 1301 with a pin shaped element 1303 occupying at least a portion of the internal lumen of cone 1301, according to some embodiments of the invention. FIG. 13B is a horizontal cross section along line AA of the nozzle. FIG. 13C shows an enlarged view of pin shaped element 1303.

In some embodiments, a distal end of tube 1305 passes into a lumen 1307 of cone 1301 which is not occupied by pin shaped element 1303. In some embodiments, other elements, for example a cylinder, may be used for occupying a portion of the nozzle, to create a lumen which may be used for flowing fluid in a specific flow pattern and/or direction.

In some embodiments, pin shaped element 1303 has a diameter smaller than the diameter of cone 1301. In some embodiments, fluid passes within lumen 1307. In some embodiments, a distance between a face of the rod portion 1309 of pin shaped element 1303 and an internal face of cone 1303 ranges between 0.2-3 mm.

In some embodiments, as seen on FIG. 13A, rod portion 1309 is shaped as a cylinder comprising a rounded elliptical tip 1315. In some embodiments, as seen on FIG. 13D, rod portion 1309 is shaped as a narrowing cone, having a sharp pointed tip 1317.

In some embodiments, a head 1311 of pin shaped element 1303 fits within cone 1301 such that an upper portion of cone 1301 is fully occupied by head 1311. Optionally, this prevents fluid from passing through.

In some embodiments, tube 1305 may be connected at its proximal end to a pipe in the handle (not shown in this figure). In some embodiments, fluid such as liquid, air, and/or abrasive powder or combinations of them may pass through tube 1305. In some embodiments, the fluid circulates within lumen 1307, for example in a helical flow. Optionally, the helical flow is caused by rod portion 1309, since fluid is forced to pass around it. In some embodiments, the fluid exits the nozzle through exit aperture 1313 in the form of an angled jet due to the helical flow.

In some embodiments, tube 1305 has an elliptical cross section 1319. Alternatively, tube 1305 has a circular cross section, a rectangular cross section, or any other shape. In some embodiments, tube 1305 twists around rod 1309, for example adjacent to the rod.

In some embodiments, as seen on 13A, cone 1301 has a narrow elongated tip portion 1315. In some embodiments, as seen on 13D, cone 1301 has a flat-shaped tip portion 1317.

Figure 14:
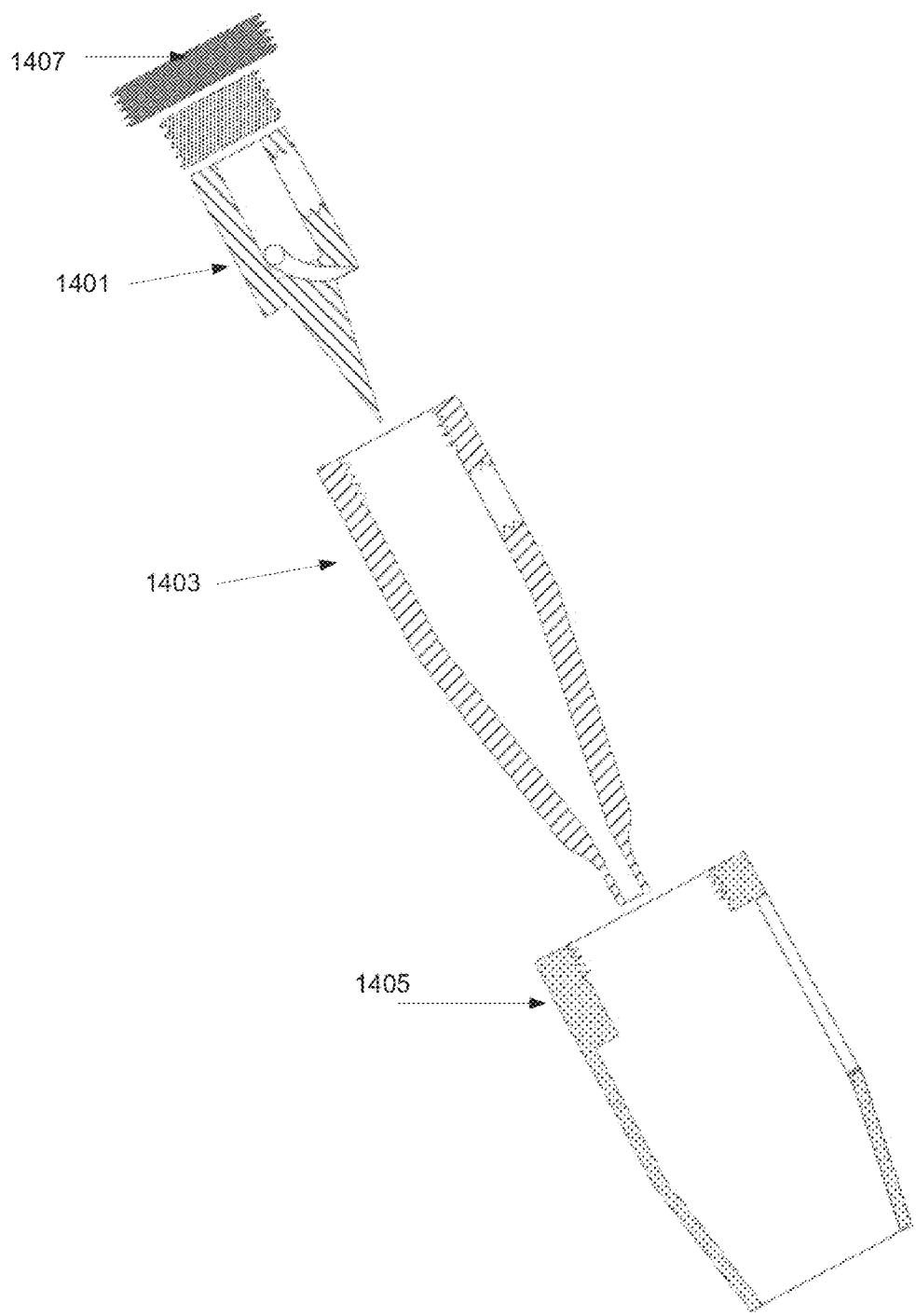
FIG. 14 shows an exemplary assembly of a nozzle, according to some embodiments of the invention.

FIG. 14 shows an exemplary assembly of a nozzle, according to some embodiments of the invention.

In some embodiments, the nozzle comprises an internal cone 1401, an external cone 1403, a suction cone 1405, and one or more lids 1407. In some embodiments, for example during manufacturing, internal cone 1401 is inserted into an external cone 1403. In some embodiments, internal cone 1401 is assembled within external cone 1403, and optionally both cones are assembled within suction cone 1405.

In some embodiments, at least two of the cones are connected by mechanical means, such as pins or screws. In some embodiments, the cones are connected by molding means, for example by casting at least two of the cones together using a designated mold. Optionally, any two and/or all cones are molded together, for example creating a nozzle made of one piece.

In some embodiments, any of the cones is detachable, for example to enable cleaning.

Figure 15:
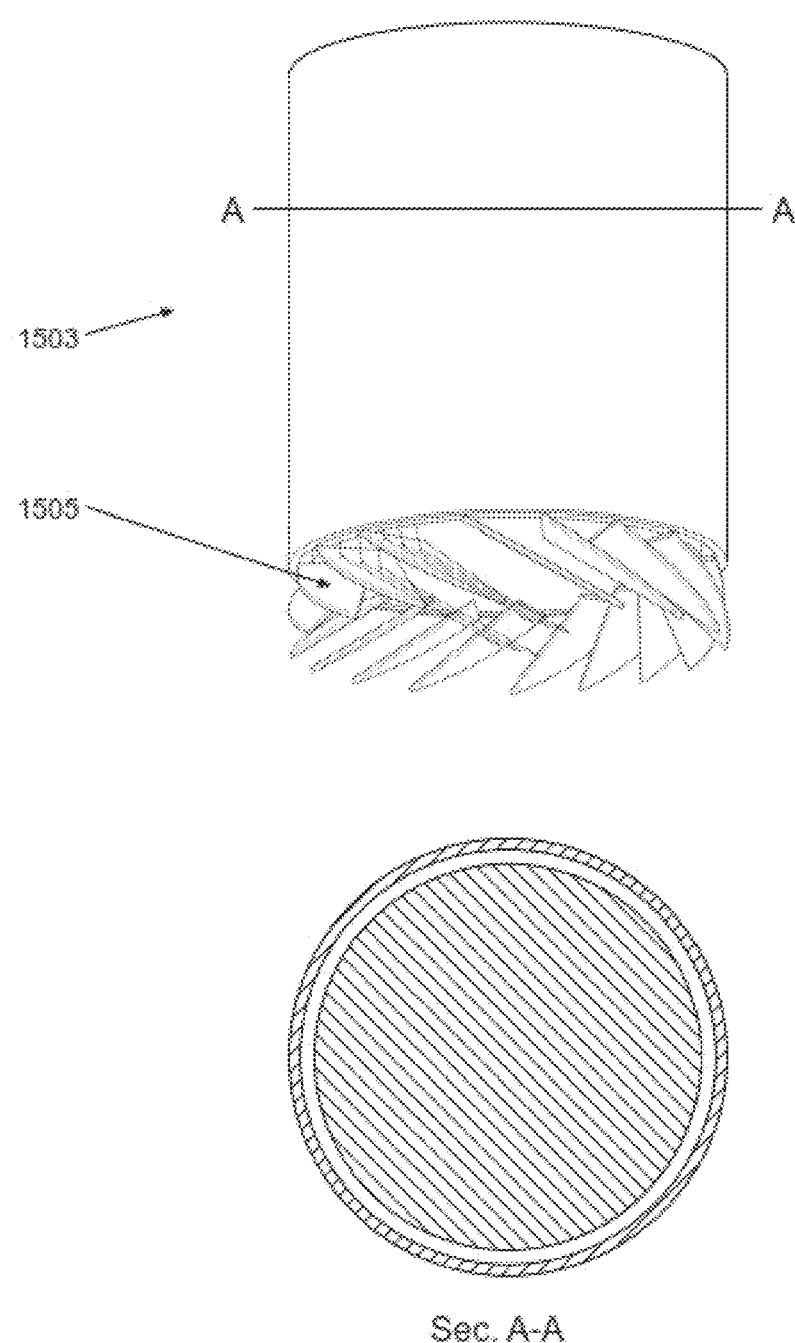
FIG. 15 is an illustration of a nozzle including exit flow shaping elements for creating the one or more angled fluid jets, according to some embodiments of the invention.

FIG. 15 is an illustration of a nozzle including exit flow shaping elements for creating the one or more angled fluid jets. In some embodiments, the exit flow shaping elements may be shaped as wings 1505.

In some embodiments, nozzle 1503 includes one or more wing elements 1505. In some embodiments, wing elements 1505 are used for diverting the fluid exiting nozzle 1503 to create one or more angled jets, for example, as previously described.

In some embodiments, the fluid passes in a parallel flow through the cylindrical nozzle 1503, and wing elements 1505 shunt the parallel fluid to an angled direction. In some embodiments, nozzle 1503 comprises parallel tubes, and wing elements 1505 are positioned at a distal end of the tubes.

In some embodiments, wing elements 1505 are configured along an exit aperture of nozzle 1503.

It is expected that during the life of a patent maturing from this application many relevant endodontic apparatuses will be developed and the scope of the term endodontic apparatuses is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

An Experiment for Testing the Feasibility of an Apparatus and Method for Endodontic Treatment using Angled Fluid Jets The inventors conducted an experiment for testing the feasibility of a system which comprises an apparatus for cleaning, abrading, and/or disinfecting a root canal as described above.

Experimental Design 41 human teeth specimens were extracted from patients. The specimens included a group of molars having 2-4 root canals, and a group of incisors having a single root canal. In total, 182 root canals were tested in the experiment. Each tooth specimen had one or various types of root canals, as indicated below.

5 types of root canals were tested: a standard root canal (53 specimens), a curved root canal (40 specimens), a sharp curved root canal (32 specimens), a root canal with an enlarged opening at the apex, ranging between 2-3 mm, which was created naturally as a result of calcification (33 specimens), and specimens with an extremely narrow root canal (24).

11 teeth specimens having 2-3 root canals each were extremely narrow, having an entrance aperture with a diameter smaller than 0.5 mm.

Immediately after the extraction, the specimens were placed in a 10% bleach solution, containing 10% chlorine and 90% water, (other solutions may also be used), to prevent dehydration of the root canals.

The following procedure was performed for each specimen. At first, an access cavity was drilled through the crown of the tooth to enable access through the pulp chamber to the root canal. An entrance to the root canal was exposed, and the specimen was placed back in the bleach solution. The specimen was then removed from the solution, and placed in a rubber mold. At this stage, the specimen was imaged using a 320 slices CT imaging device. Optionally, other imaging devices may be used.

An apparatus and system for example as described in FIG. 8 above were used for cleaning, abrading, and disinfecting each of the specimens. A nozzle of the apparatus was inserted through the pulp chamber and positioned such that an exit aperture of the nozzle was configured vertically above the entrance to a root canal, at an approximate distance of 1-3 mm.

The fluid used for the treatment of the root canals contained water, air, and glass powder (used as an abrasive powder). The pressures used were a water pressure of 80 PSI, and an air pressure of 80 PSI. The fluid passed through the pipeline of the system, for example through pipes in the handle of the apparatus, reaching the nozzle and exiting through the exit aperture in the form of angled fluid jets, as previously described.

Cleaning, abrading and disinfecting of the root canal of each specimen was achieved by the flow of fluid advancing along the root canal wall, removing organic substance such as nerve tissue, pulp tissue, and/or debris, as previously described.

The treatment duration for each of the specimens was determined according to parameters such as the existence of a narrowing portion, the existence of curvature, the length of the root canal, and/or other parameters or combinations of them. The treatment duration used in this experiment was 15 seconds (applied to 13 specimens), 30 seconds (applied to 15 specimens), and 45 seconds (applied to 13 specimens). Optionally, other durations may be used.

Imaging of each specimen using a 320 slices CT imaging device was performed again at the end of the process.

Each specimen was tested for apex penetration (referred to in this example as further widening of a natural, normal opening of the apex), grade of apex penetration (if occurred), penetration along the canal wall, and the thickness of the eroded layer.

To prove that the root canals of the specimen are clean, an electro-scan microscope image was acquired from each specimen, as will be further explained.

Data Analysis and Results

FIG. 16A-B is a table of the experiment results. The table shows that in all tested root canals, the apex was not penetrated (i.e. an initial natural opening was not widened). The table also shows that in all tested root canals, the root canal wall was not penetrated as well. The thickness of the removed dentin layer ranged between 100-200 μm for all tested root canals.

Figure 17:
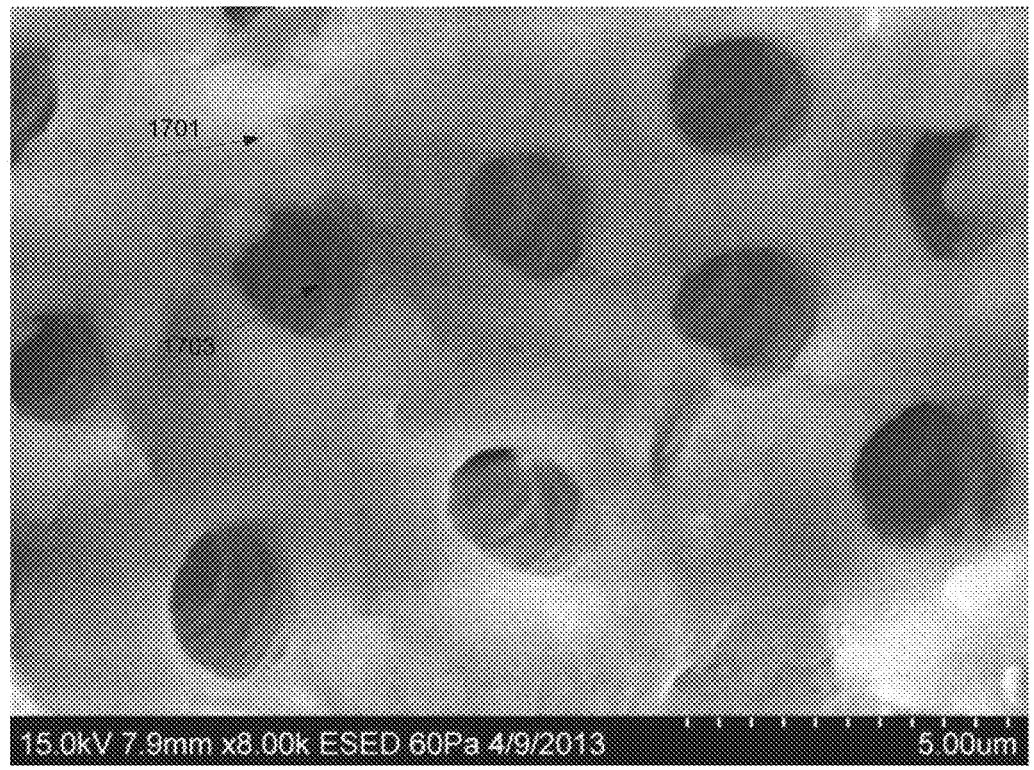
FIG. 17 is an image of a dentin layer and dentinal tubules taken by an electro scan microscope after treating a root canal using the apparatus.

FIG. 17 shows an image of the dentin layer and dentinal tubules of one of the specimens, taken at the end of the experiment described above. This image was taken by an electro scan microscope, using a magnification of ×5000.

Before acquiring the image, the specimen was stored in the bleach solution. Once the specimen was removed from the solution, it was sliced along a longitudinal cross section, to expose the internal lumen of the root canal. This exemplary image shows that the dentin layer 1701 and the tubules 1703 shave been cleaned and cleared by the flow of fluid, and do not have a smear layer.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus for endodontic treatment comprising a nozzle, wherein:
said nozzle comprises:
a tip configured and sized to be inserted through a pulp chamber of a tooth;

an inner tapering portion and a surrounding outer tapering portion separated by a lumen; and wherein said nozzle is connected to an input pipeline;

wherein said nozzle is shaped so that fluid supplied by said input pipeline travels through said lumen to create a beam comprising at least one fluid jet where an axis of said fluid jet is at an angle to a vertical axis of said nozzle and said axis of said fluid jet does not intersect said vertical axis of said nozzle, so that said beam flows along a wall of a root canal connected to said pulp chamber, to remove soft tissue.

2. The apparatus according to claim 1, wherein said inner tapering portion is an internal cone and said surrounding outer tapering portion is an external cone, which cones defining said lumen between them for said fluid to flow through.

3. The apparatus according to claim 2, wherein said nozzle comprises a tube extending between a lumen of said internal cone and said lumen between said internal cone and said external cone.

4. The apparatus according to claim 2, wherein said fluid circulates in a helical flow through said lumen for exiting the nozzle in an angle.

5. The apparatus according to claim 1, wherein said nozzle comprises channels for creating said at least one angled jet.

6. The apparatus according to claim 1, wherein said at least one fluid jet comprises liquid and at least one of gas, and abrasive powder.

7. The apparatus according to claim 6, wherein said gas is air, and said at least one fluid jet comprises between 50-95% air and between 5-50% liquid.

8. The apparatus according to claim 7, wherein said nozzle is shaped so that said at least one fluid jet exits said nozzle as an aerosol.

9. The apparatus according to claim 6, wherein said liquid and said at least one of said abrasive powder and said gas are mixed together in said nozzle.

10. The apparatus according to claim 9, wherein said liquid and said at least one of said abrasive powder and said gas flow through said lumen.

11. The apparatus according to claim 10, wherein said nozzle comprises a tube extending into said lumen of said nozzle.

12. The apparatus according to claim 11, wherein at least one of liquid, gas, and abrasive powder are passed into said nozzle through said tube.

13. The apparatus according to claim 1, wherein said apparatus is connected to an air compressor with a pressure ranging between 5-300 PSI.

14. The apparatus according to claim 1, wherein said apparatus is connected to a fluid tank which provides fluid at a volumetric flow rate ranging between 0.1-100 ml/second.

15. The apparatus according to claim 1, wherein said angled jet has tangential and vertical velocity components in respect to said root canal wall.

16. The apparatus according to claim 1, wherein said apparatus further comprises a suction cone for collecting returning fluid and debris, wherein said suction cone has a tip sized to fit within a pulp chamber of a tooth.

17. The apparatus according to claim 1, wherein said nozzle comprises one or more exit flow shaping element for creating said at least one angled jet.

18. The apparatus according to claim 1, wherein said at least one jet is a plurality of jets.

19. The apparatus of claim 1, wherein a diameter of said tip is 0.3-2 mm.

20. The apparatus of claim 19, wherein said at least one fluid jet is a plurality of said jets, where each jet has an axis which does not intersect said vertical axis of said nozzle and is at an angle to said vertical axis of said nozzle.

21. The apparatus of claim 19, wherein said beam flowing along said wall of said root canal removes a layer of tissue 100-200μm thick in 15-45 seconds.

22. The apparatus of claim 1, said nozzle includes a slanted tube where an exit of said slanted tube is positioned within said lumen;

wherein said slanted tube is sized and angled and said lumen is sized and angled such that fluid flowing from said slanted tube into said lumen flows in a helical path through said lumen thereby creating said beam.

23. A system for endodontic treatment comprising:
a liquid tank,
an air compressor,
an input pipeline; and
a nozzle comprising:
a tip configured and sized to be inserted through a pulp chamber of a tooth:
an inner tapering portion and a surrounding outer tapering portion separated by a lumen; and
wherein said input pipeline passes through a handle to connect said at least one of said liquid tank and said air compressor to said nozzle;
wherein said nozzle is shaped so that fluid supplied by said input pipeline travels through said lumen to create a beam comprising at least one fluid jet where an axis of said fluid jet is at an angle to a vertical axis of said nozzle and said axis of said fluid jet does not intersect said vertical axis of said nozzle, so that said beam flows along a wall of a root canal connected to said pulp chamber, to remove soft tissue.

24. The system according to claim 23, wherein said system is electrically controlled by using a control panel and electric circuit.

* * * * *